United States Patent
Ohura et al.

(10) Patent No.: US 8,685,220 B2
(45) Date of Patent: *Apr. 1, 2014

(54) CAPILLARY ELECTROPHORESIS APPARATUS

(75) Inventors: Takeshi Ohura, Hitachinaka (JP); Ryoji Inaba, Hitachinaka (JP); Yoshitaka Kodama, Hitachinaka (JP); Hiromi Yamashita, Ishioka (JP); Manabu Akiba, Mito (JP); Tomohiro Shoji, Hitachinaka (JP)

(73) Assignee: Hitachi High-Technologies Corporation, Tokyo (JP)

( * ) Notice: Subject to any disclaimer, the term of this patent is extended or adjusted under 35 U.S.C. 154(b) by 0 days.

This patent is subject to a terminal disclaimer.

(21) Appl. No.: 13/559,445

(22) Filed: Jul. 26, 2012

(65) Prior Publication Data

US 2012/0292189 A1 Nov. 22, 2012

Related U.S. Application Data

(63) Continuation of application No. 12/344,053, filed on Dec. 24, 2008, now Pat. No. 8,252,162.

(30) Foreign Application Priority Data

Dec. 28, 2007 (JP) ................. 2007-341018

(51) Int. Cl.
*C02F 1/40* (2006.01)
*C02F 1/48* (2006.01)
*C02F 11/00* (2006.01)
*G01N 27/00* (2006.01)
*C25B 13/00* (2006.01)
*C25B 11/00* (2006.01)
*C25B 9/00* (2006.01)

(52) U.S. Cl.
USPC ........... 204/601; 204/602; 204/603; 204/604; 204/605

(58) Field of Classification Search
USPC ........ 204/600–616, 451–455; 220/23.2, 23.4, 220/480; 73/864.59
See application file for complete search history.

(56) References Cited

U.S. PATENT DOCUMENTS

| | | | |
|---|---|---|---|
| 5,147,522 | A | 9/1992 | Sarrine |
| 5,286,959 | A | 2/1994 | Demachi |

(Continued)

FOREIGN PATENT DOCUMENTS

| | | |
|---|---|---|
| JP | 01-301167 A | 12/1989 |
| JP | 04-063065 U | 5/1992 |

(Continued)

OTHER PUBLICATIONS

Japanese Office Action, with English translation, issued in Japanese Patent Application No. 2007-341018, dated Oct. 18, 2011.

(Continued)

*Primary Examiner* — Luan Van
*Assistant Examiner* — Maris R Kessel
(74) *Attorney, Agent, or Firm* — McDermott Will & Emery LLP

(57) ABSTRACT

The invention provides a capillary electrophoresis apparatus which can improve the operability and measuring speed. According to the invention, a sensor for identifying the type of sample containers is fixed at the position away from a capillary anode electrode. The sensor is made to be closer to the sample containers by moving a moving stage so that the sample containers disposed on the moving stage can be identified by the sensor. A fixing apparatus for fixing at least a pair of sample containers is provided on the moving stage.

4 Claims, 14 Drawing Sheets

(56) References Cited

U.S. PATENT DOCUMENTS

| | | |
|---|---|---|
| 7,767,154 B2 | 8/2010 | Nichols et al. |
| 2002/0003091 A1 | 1/2002 | Kojima et al. |
| 2004/0000550 A1* | 1/2004 | Taccolini et al. ............ 220/23.4 |
| 2004/0173460 A1 | 9/2004 | Yamamoto et al. |
| 2006/0006066 A1 | 1/2006 | Yamazaki et al. |

FOREIGN PATENT DOCUMENTS

| | | |
|---|---|---|
| JP | 2001-324474 | 11/2001 |
| JP | 2002-090374 A | 3/2002 |
| JP | 2003-344357 | 12/2003 |
| JP | 2006-058312 A2 | 3/2006 |
| JP | 3950417 B2 | 8/2007 |
| JP | 4086065 B2 | 5/2008 |
| WO | WO 02090968 A1 | 11/2002 |

OTHER PUBLICATIONS

Entire Prosecution of U.S. Appl. No. 12/344,053, to Takeshi Ohura et al. on Dec. 24, 2008, entitled, "Capillary Electrophoresis Apparatus."

* cited by examiner

CAPILLARY ELECTROPHORESIS APPARATUS

RELATED APPLICATIONS

This application is a Continuation of U.S. application Ser. No. 12/344,053, filed on Dec. 24, 2008 now U.S. Pat. No. 8,252,162, claiming priority of Japanese Patent Application No. 2007-341018, filed on Dec. 28, 2007, the entire contents of each of which are hereby incorporated by reference.

BACKGROUND OF THE INVENTION

1. Field of the Invention

The invention relates to a capillary electrophoresis apparatus which separates and analyzes samples such as DNA and protein by electrophoresis, particularly to an autosampler (apparatus for automatically transporting sample containers) which transports containers holding a solution.

2. Description of the Related Art

With reference to the capillary electrophoresis apparatus, a component of a sample is separated by introducing the sample into a capillary filled with separation media and applying a high voltage to both ends of the capillary. Sample plates holding samples have various forms. Generally, the sample plate having 96 wells (arranged in an 8×12 matrix with a pitch of 9 mm) and the sample plate having 384 wells (arranged in a 16×24 matrix with a pitch of 4.5 mm) are used.

An example of a sample plate assembly is described in Japanese Patent Application Laid-Open Publication No. 2001-324474 (JP-A-2001-324474). The sample plate assembly has a structure in which the sample plate on which a septer having a function of preventing evaporation of the samples is mounted is sandwiched between an upper-side septer holder and a lower-side adapter.

A mechanism in which the sample plate assembly is held by a gripper is disclosed in Japanese Patent Application Laid-Open Publication No. 2003-344357 (JP-A-2003-344357). The gripper holds the sample plate assembly directly, thereby allowing the sample plate assembly to be held.

Recently, there has been a demand for improvement in operability and measuring speed of the capillary electrophoresis apparatus. In order to satisfy the demand, it is necessary to simplify operation for disposing the sample plate assembly on a moving stage of the autosampler.

The autosampler transports each container which contains solutions such as a sample solution, buffer solution, assy solution, cleaning liquid, and waste liquid to a capillary anode electrode. The capillary anode electrode is formed on a capillary electrode. The capillary electrode has a structure in which the end of the capillary is integrated with an electrode for electrophoresis. The capillary electrode is fixed on a load header. On the other hand, each container is disposed on the moving stage of the autosampler and is movable in the direction of three dimensions of X-Y-Z. Each container is first transported to under the capillary anode electrode by the autosampler and then moved upward. As a result, contact of the capillary electrode with the solution is realized.

When the sample plate is transported by the autosampler, a type of sample plate needs to be recognized. Therefore, a sample plate identification mechanism for identifying the type of sample plate is provided in the autosampler. In the sample plate identification mechanism described in JP-A-2001-324474, a detection plate is provided on the bottom surface of the adapter and a photo interrupter is provided on the upper surface of the moving stage of the autosampler. When the sample plate assembly is disposed on the moving stage, the photo interrupter is engaged with the detection plate. The light from the photo interrupter is blocked by the detection plate. As a result, the type of sample plate can be detected. A type of identifiable sample plate can be increased by increasing the numbers of the photo interrupters and the detection plates.

The sample plate identification mechanism using both the photo interrupter and the detection plate has an advantage that the type of sample plate can always be identified while the sample plate assembly is disposed on the moving stage. For example, the type of sample plate is analyzed by a sample processing program and then the analyzed result can be presented to an operator. When the type of sample plate cannot be analyzed by the sample processing program, wrong measurements can be prevented by stopping the operation of the autosampler.

However, the photo interrupter is exposed on the moving stage in the sample plate identification mechanism using both the photo interrupter and the detection plate. In the capillary electrophoresis apparatus, the operator places containers containing liquids such as a buffer solution, cleaning liquid, and waste liquid on the moving stage. For that reason, liquids may fall on the photo interrupter due to the operator's carelessness. Further, a cable for supplying an electric power and transmitting a signal is connected with the photo interrupter. The cable moves together with the moving stage whenever the moving stage moves.

As described above, there is a demand for improvement in operability and measuring speed of the capillary electrophoresis apparatus. In order to satisfy the demand, the development of the sample plate identification mechanism in which it is not necessary to form the photo interrupter on the moving stage has been required.

SUMMARY OF THE INVENTION

According to the invention, there is provided a capillary electrophoresis apparatus which can improve the operability and measuring speed.

According to the invention, a sensor for identifying the type of the sample containers is fixed at the position away from the capillary anode electrode. The sensor is made to be closer to the sample containers by moving the moving stage so that the sample containers disposed on the moving stage can be identified by the sensor. A fixing apparatus for fixing at least a pair of sample containers is provided on the moving stage.

According to the invention, there can be provided the capillary electrophoresis apparatus which can improve the operability and measuring speed.

DESCRIPTION OF REFERENCE NUMERALS

Figure 1:
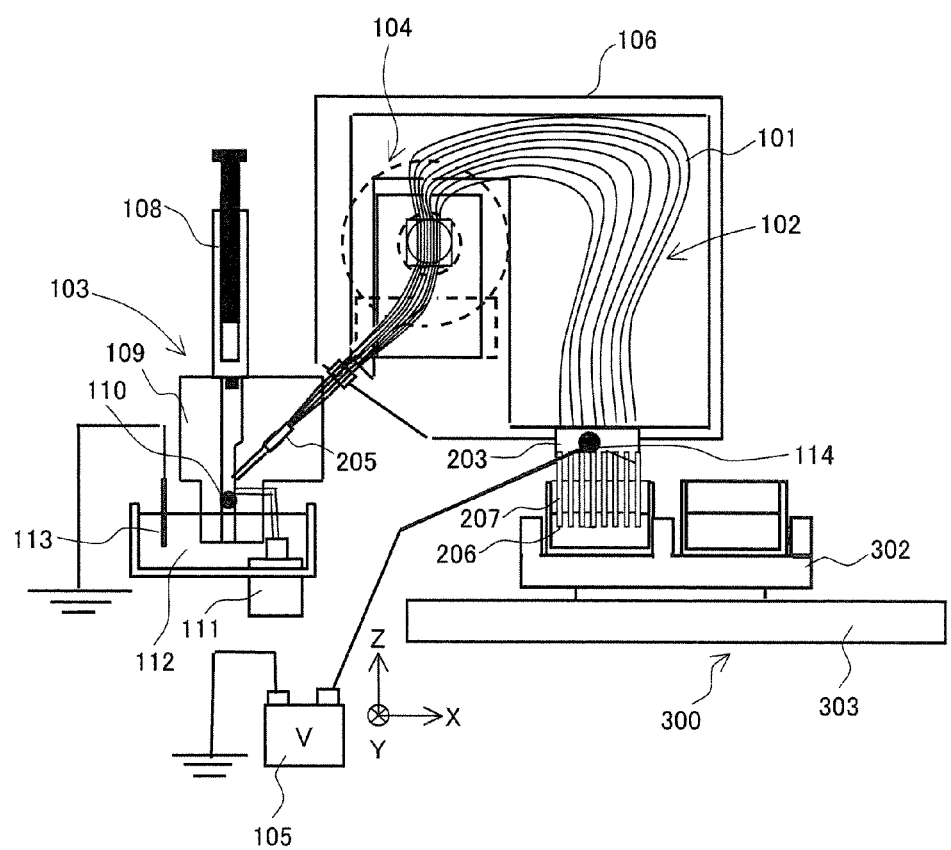
FIG. 1 is a diagram illustrating an outline of the capillary electrophoresis apparatus according to the invention.

101 Capillary
102 Capillary array
103 Pump mechanism
104 Optical system
105 High voltage power supply
106 Oven
108 Syringe
109 Block
110 Check valve
111 Polymer container
112 Cathode buffer container
113 Cathode electrode
114 Anode electrode
203 Load header
205 Capillary head
206 capillary anode electrode
207 Capillary electrode
300 Autosampler
302 Moving stage
303 Linear guide
310 Fixed portion
311 Photo interrupter
315 Housing
316 Door
317 Opening-and-closing detection mechanism
400 Fixation mechanism
401 Movable hook
402 Lever portion
403 Claw
404 Shaft
405 Torsion spring
411 Movable hook
412 Lever portion
413 Claw
414 Shaft
415 Torsion spring
421 Movable hook
422 Lever portion
423 Claw
424 Shaft
425 Torsion spring
431 Movable hook
432 Lever portion
433 Pressing portion
434 Shaft
435 Torsion spring
501 Sample plate assembly
501a-501d Side surface
502 Sample plate assembly
502a-502d Side surface
503 Buffer container
504 Cleaning container
505 Waste liquid container
3021, 3021A, 3021B Convex portion
3022, 3023, 3024 Fixed hook
4106 Concave portion
4302 Convex portion
5011 Sample
5012 Sample plate
5013 Septa
5014 Clip
5015 Adapter
5017 Detection plate
5018, 5018A, 5018B Concave portion
5021, 5022 Hole
5031 Buffer solution
5033 Septa
5033a Hole
5041 Cleaning liquid
5043 Septa
5043a Hole

DESCRIPTION OF THE PREFERRED EMBODIMENT

FIG. 1 illustrates an outline of the capillary electrophoresis apparatus according to the embodiment. The capillary electrophoresis apparatus according to the embodiment has a capillary array 102 including a single or a plurality of capillaries 101, a pump mechanism 103 for injecting separation media into the capillaries 101, an optical system 104 for irradiating samples in the capillaries 101 with a light and detecting the fluorescence of the samples, a high voltage power supply 105 for applying a high voltage to the capillaries 101, an oven 106 for keeping the capillaries 101 at a constant temperature, and an autosampler 300 for transporting containers containing the samples and solutions.

The capillaries 101 are exchangeable members, which are replaced when a method of measurement is changed or breakage and quality degradation are observed in the capillaries 101. The capillaries 101 comprise glass tubes having an inner diameter of tens to hundreds of microns and an outer diameter of hundreds of microns and the surface thereof are coated with polyimide. The capillaries 101 are filled with separation media which gives a migration time difference to samples such as DNA and protein at the time of electrophoresis.

Although there are fluid and non-fluid separation media, a fluid polymer is used in the embodiment.

A capillary head 205 is provided at one end of the capillaries 101 and a capillary anode electrode 206 is formed at the other end thereof. The capillary head 205 is the end portion of the bundled capillaries 101 and has a function of connecting the pump mechanism 103 and the capillaries 101. The capillary anode electrode 206 is in contact with the samples and solutions. At the side of the capillary anode electrode, the capillaries 101 are fixed by a load header 203.

A anode electrode 114 and a capillary electrode 207 which is a tubular member made of metal are mounted on the load header 203. The anode electrode 114 and the capillary electrode 207 are conducting. The capillary anode electrode 206 penetrates the capillary electrode 207 and protrudes from the end thereof.

The optical system 104 comprises an illumination system and a detection system. The optical system 104 has a function for irradiating a portion from which a polyimide film of the capillaries 101 is removed, namely, a detection portion with an exciting light. The detection system has a function for detecting the fluorescence from the samples in the detection portion of the capillaries 101. The samples are analyzed on the basis of the light detected by the detection system.

The pump mechanism 103 has a syringe 108, a block 109, a check valve 110, a polymer container 111, and an cathode buffer container 112. A passage in the block 109 is connected with the capillaries 101 by connecting the capillary head 205 with the block 109. The polymer in the polymer container 111 is charged into the capillaries 101 via the passage in the block 109 or refilled by operating the syringe 108. The refilling of the polymer in the capillaries 101 is carried out for each measurement in order to improve the performance of the measurement.

An cathode electrode 113 is disposed in the cathode buffer container 112. The high voltage power supply 105 applies a high voltage between the cathode electrode 113 and the anode electrode 114.

The oven 106 keeps the temperature of the capillaries constant by sandwiching a capillary array 102 using a temperature control plate on which a heat insulating material and a heater are mounted, in a planar shape. A temperature sensor for feedback is mounted on the temperature control plate. The edge of the capillary head 205 can be fixed at a desired position by fixing the load header 203 to the oven 106.

The autosampler 300 has three electric motors for moving the moving stage 302 and a linear guide 303. Here, as shown in the drawings, a Z-axis is taken in a vertically-upward direction along a plane on which the capillary array 102 is disposed, an X-axis is taken in a horizontal direction, and a Y-axis is taken in a thickness direction of the plane on which the capillary array 102 is disposed. The moving stage is movable in an up-and-down direction (Z-axis direction), in a right-and-left direction (X-axis direction), and in a depth direction (Y-axis direction). The moving stage 302 carries a buffer container, a cleaning container, a waste liquid container, and a sample plate to the capillary anode electrode 206, as needed.

Figure 2:
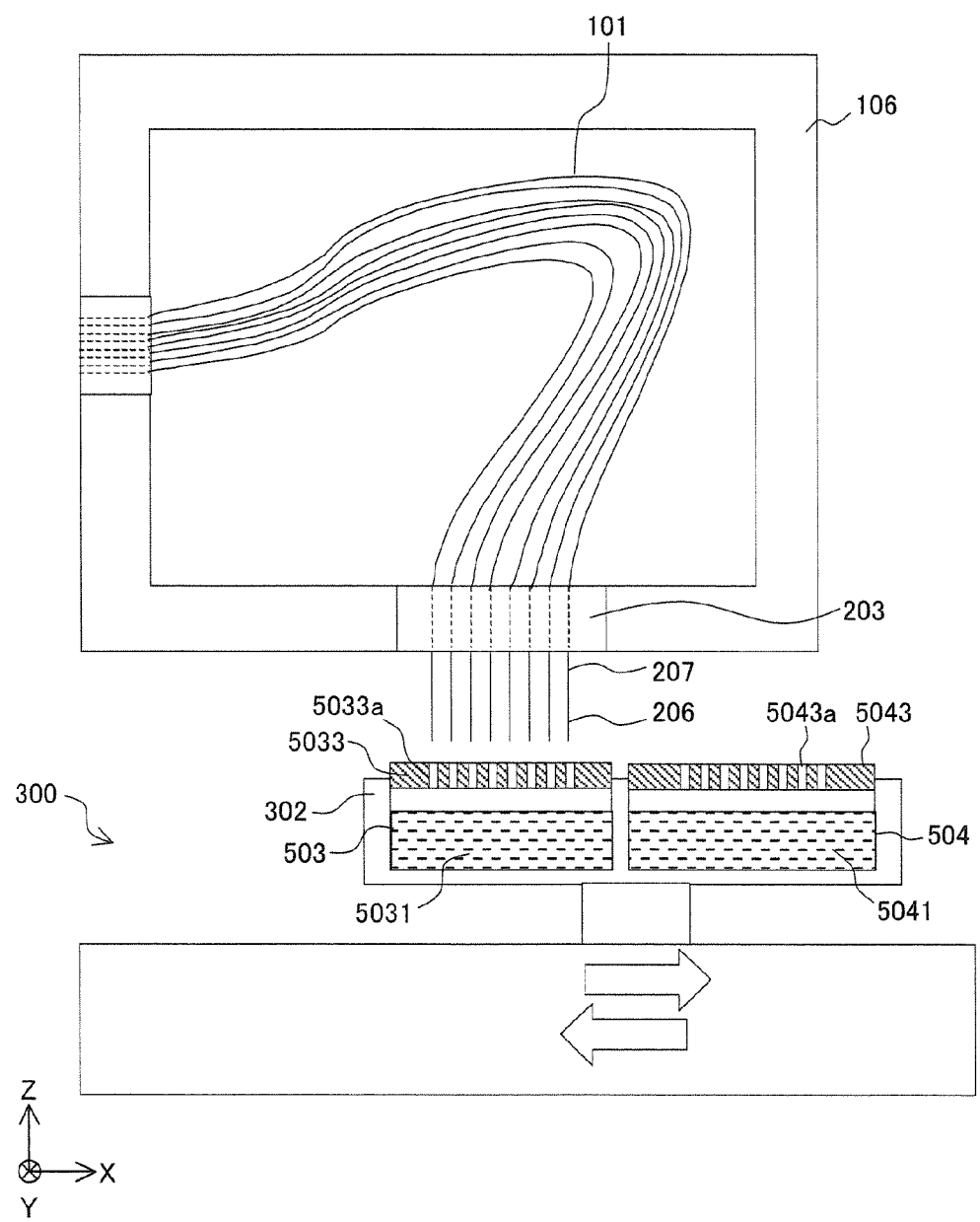
FIG. 2 is an explanatory diagram explaining the operation of the autosampler.

The operation of the autosampler will be described with reference to FIGS. 2 and 3. The capillaries 101 of the capillary electrophoresis apparatus, the oven 106, and the autosampler 300 are shown in FIG. 2, however, the optical system and the pump mechanism are not shown herein. The load header 203 is mounted at a lower end of the oven 106. The capillaries 101 are fixed to the load header 203. The capillary electrode 207 comprising the tubular member is mounted on the load header 203. The capillaries 101 penetrate the capillary electrode 207 and the capillary anode electrode 206 is protruded from the lower end.

A buffer container 503 which holds a buffer solution 5031 for electrophoresis and a cleaning container 504 which holds the cleaning liquid 5041 are disposed on the moving stage 302 of the autosampler. The buffer container 503 and the cleaning container 504 are covered with septa 5033 and 5043. Holes 5033a and 5043a are formed on the septa 5033 and 5043.

In this regard, the sample container holding the sample and the waste liquid container holding the waste liquid are disposed on the moving stage 302 and these containers are arranged with the buffer container 503 and the cleaning container 504. Thus, they are not illustrated herein.

FIG. 2 illustrates a state in which the buffer container 503 has been transported just under the capillary anode electrode 206 by the autosampler 300. That is, the buffer container 503 is transported just under the capillary anode electrode 206 by moving the moving stage 302 in back-and-forth and right-and-left directions. Subsequently, the following will be described with reference to FIG. 3.

Figure 3:
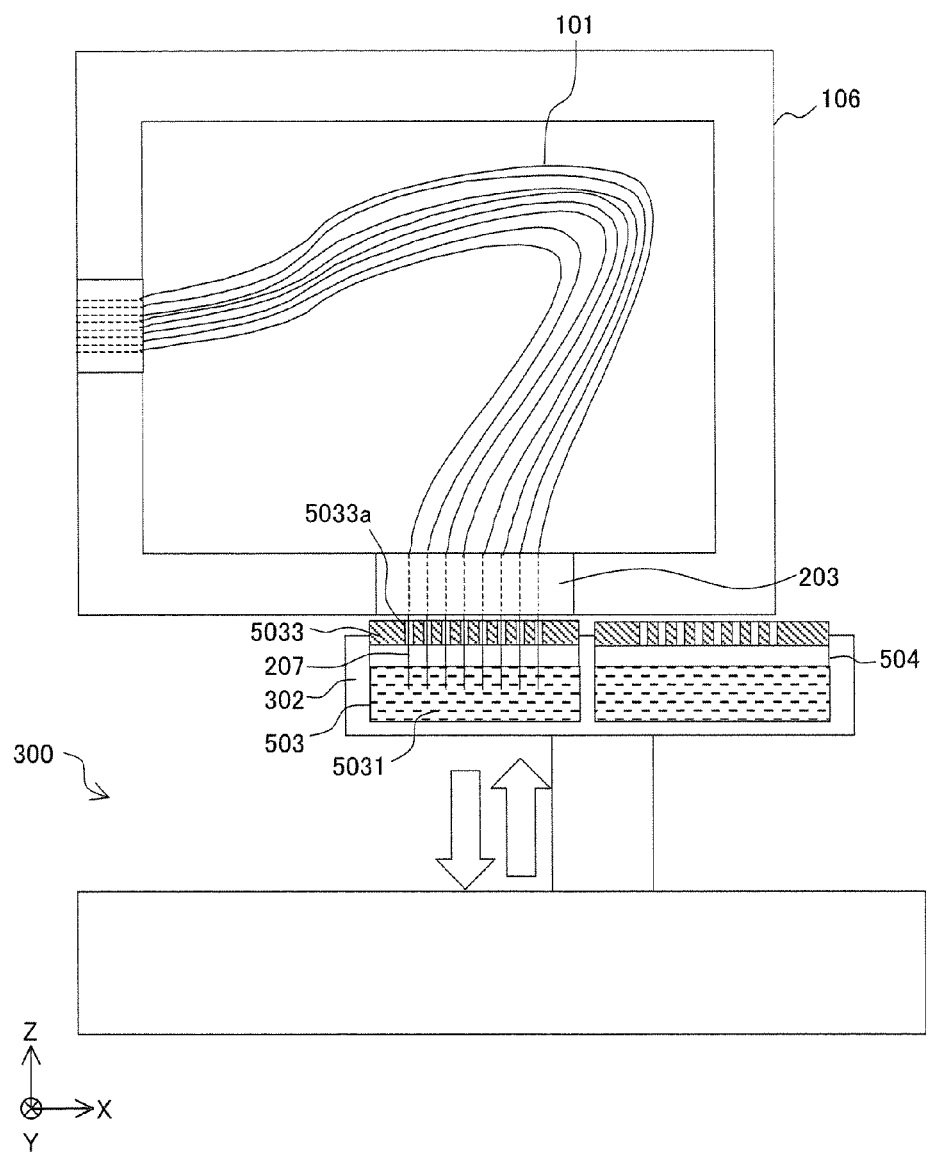
FIG. 3 is an explanatory diagram explaining the operation of the autosampler.

As shown in FIG. 3, the moving stage 302 is moved upward. Thus, the capillary electrode 207 penetrates the hole 5033a of the septa 5033 of the buffer container 503 and is immersed in the buffer solution 5031.

Figure 4A:
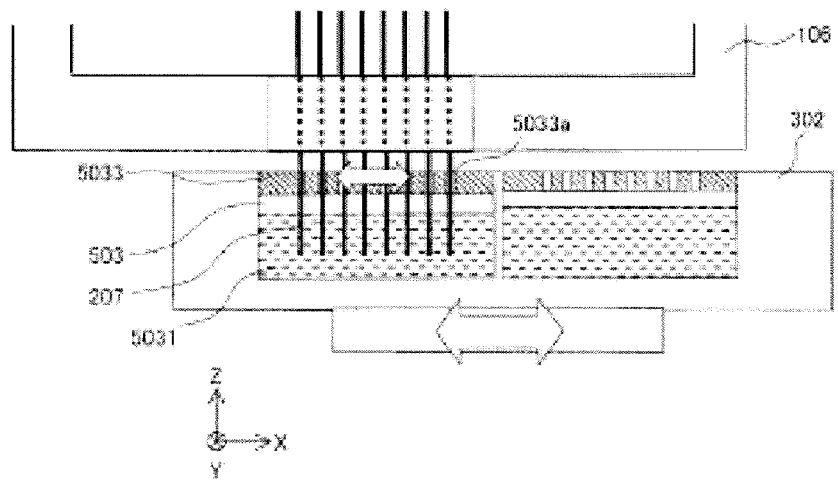
FIG. 4A is an explanatory diagram explaining an example of a fixation mechanism of a conventional autosampler.

A conventional autosampler will be described with reference to FIG. 4A. FIG. 4A illustrates a principal part of the autosampler in related art. The capillary electrode 207 penetrates the hole 5033a of the septa 5033 of the buffer container 503 and is immersed in the buffer solution 5031. In order to ensure a sealing property of the buffer container 503, the difference between an inner diameter of the hole 5033a of the septa 5033 and an outer diameter of the capillary electrode 207 is slight.

For the purpose of achieving a separation performance of capillary electrophoresis, it is necessary to prevent gel separation media charged in the capillaries from being dried. Therefore, it is necessary that the capillary anode electrode is always in contact with the solution. When the measurement is completed, the power supply of the capillary electrophoresis apparatus is turned off. Even when the power supply is turned off, the capillary electrode 207 is immersed in the buffer solution 5031 to prevent gel separation media in the capillaries from being dried. That is, the capillary electrode 207 is left in contact with the buffer solution 5031.

Vibrations from the outside are applied to the capillary electrophoresis apparatus in response to various causes or conditions. Examples of the cause include transport of the apparatus and earthquake occurrence. Vibrations occur when the measurement is performed on a ship or in a car. Vibrations from the outside may be applied when the power supply of capillary electrophoresis apparatus is turned on, however, they may be applied when the power supply is turned off.

Here, when the power supply of the capillary electrophoresis apparatus is turned off, vibrations from the outside are applied to the capillary electrophoresis apparatus. At this time, an electric power is not supplied to the motor which drives the autosampler. Therefore, when vibrations from the outside are given, the moving stage of the autosampler cannot be kept in a static state.

When the moving stage cannot be kept in the static state, the containers on the moving stage are moved. Thus, the capillary electrode interferes with the penetration hole of the septa, which may cause the septa to be broken. When the number of the capillary electrode is large (for example, 48 or 96), vibrations from the outside can be distributed across a plurality of the capillary electrodes. Thus, the load on one capillary electrode is low. For that reason, the breakage of the capillary electrode can be avoided. However, when the number of the capillary electrodes is small, the load on one capillary electrode is high, which is more likely to cause the breakage.

In order to solve these problems, lead screw mechanisms such as sliding screws and ball screws are conventionally used for a drive portion of the autosampler. Particularly, the friction of the screw surface and the load in a screw shaft direction are distributed by using a screw with a small lead angle. Thus, the moving stage can be maintained in the static state.

Recently, there has been an increasing need for the reduction in size and weight of the capillary electrophoresis apparatus. Further, in order to improve throughput, it is necessary to speed up transport. According to the invention, belt drivings such as a toothed belt and a steel belt are used for the autosampler.

However, the belt drivings are easily affected by vibrations from the outside. It is difficult to maintain the autosampler in the static state. According to the autosampler of the invention, there is provided a structure which can avoid the effect of vibrations from the outside.

Figure 4B:
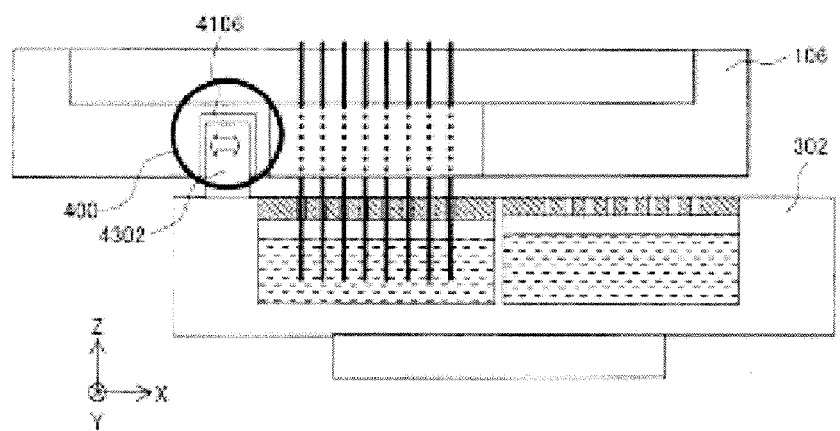
FIG. 4B is an explanatory diagram explaining an example of a fixation mechanism of the autosampler according to the invention.

An example of the autosampler according to the invention will be described with reference to FIG. 4B. In the autosampler of the embodiment, a fixation mechanism 400 which maintains the moving stage in the static state even when vibrations from the outside are given is provided. The fixation mechanism 400 has a convex portion 4302 provided on the moving stage 302 of the autosampler and a concave portion 4106 provided on the oven 106. The moving stage 302 is fixed to the oven 106 by engaging the convex portion 4302 with the concave portion 4106. That is, even if vibrations from the outside are applied when the power supply is turned off, the moving stage 302 can be kept in the static state. The convex portion 4302 may comprise a pin. The concave portion 4106 has a mechanism which houses and holds the pin. Incidentally, the concave portion may be provided on the moving stage 302 of the autosampler and the convex portion may be provided on the oven 106.

Figure 5A:
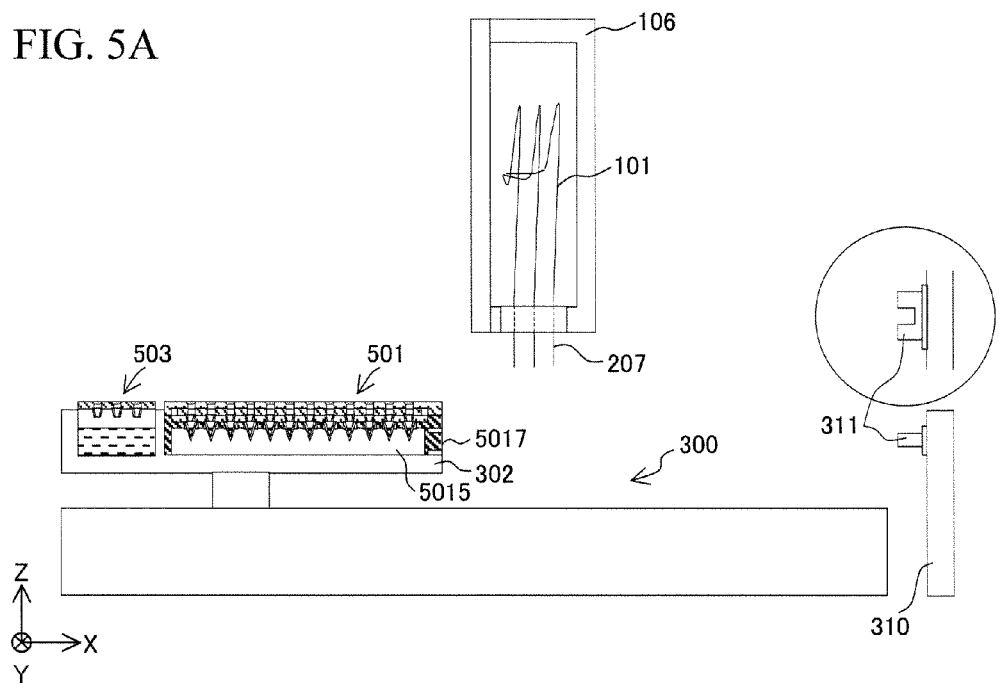
FIGS. 5A and 5B are explanatory diagrams explaining an example of the sample plate identification mechanism of the autosampler according to the invention.
Figure 5B:
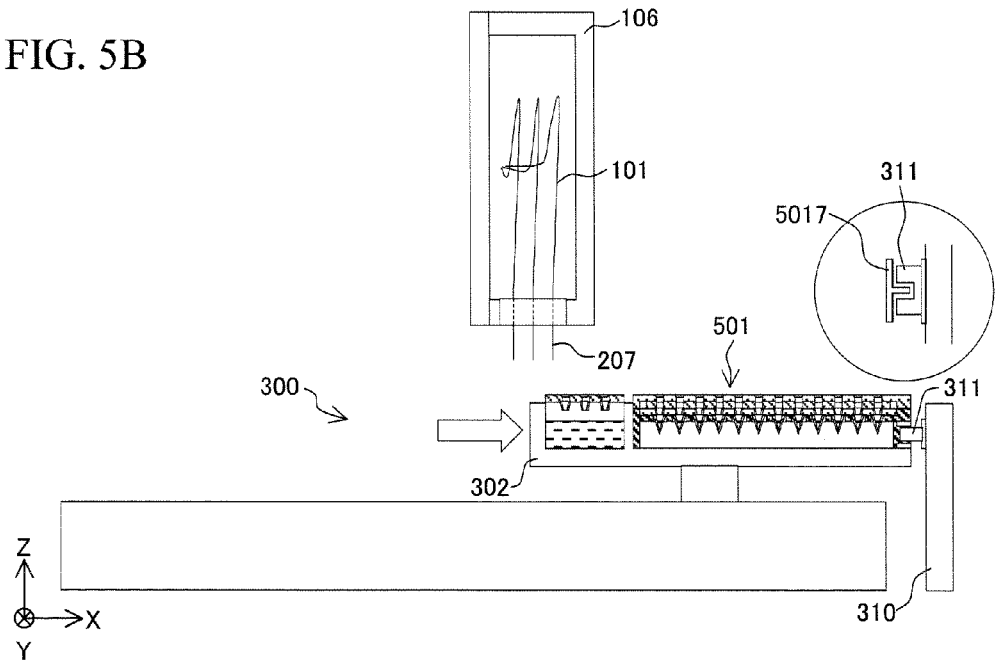

The example of the autosampler according to the invention will be described with reference to FIGS. 5A and 5B. FIG. 5A shows a cross section structure in which the oven and the autosampler according to the invention are cut along a Y-Z plane. A sample plate assembly 501 and the buffer container 503 are disposed on the moving stage 302.

The sample plate identification mechanism for detecting the type of sample plate is provided in the autosampler. The sample plate identification mechanism comprises the detection plate and the photo interrupter. In the conventional sample plate identification mechanism, a plurality of detection plates are provided on the bottom surface of the sample plate assembly 501 and a plurality of photo interrupters are disposed on the upper surface of the moving stage 302. When the sample plate assembly 501 is disposed on the moving stage 302, the photo interrupter is engaged with the detection plate.

The photo interrupter typically has a detection groove for receiving the detection plate and a light-emitting portion and a light-receiving portion are provided on both sides of the detection groove. When the detection plate is inserted between the light-emitting portion and the light-receiving portion, the light from the light-emitting portion is shielded by the detection plate and the light is not received by the light-receiving portion. When the detection plate is not inserted between the light-emitting portion and the light-receiving portion, the light from the light-emitting portion is received by the light-receiving portion. When one photo interrupter is used, there are light shielding and transmitting conditions as for the photo interrupter. That is, two kinds of sample plates; one on which the detection plate is provided and the other on which the detection plate is not provided can be identified.

When three photo interrupters are used, there are light shielding and transmitting conditions as for each of the photo interrupters. Therefore, seven types of sample plates can be identified (one type in a state that the photo interrupter is not provided on the moving stage). The type of identifiable sample plate can be increased by increasing the numbers of the photo interrupters and the detection plates.

The photo interrupter is exposed on the moving stage 302 in the conventional sample plate identification mechanism. In the capillary electrophoresis apparatus, the operator places containers containing liquids such as a buffer solution, cleaning liquid, and waste liquid on the moving stage. For that reason, liquids may fall on the photo interrupter due to the operator's carelessness. As a result, the failure is caused by an electric short-circuit.

The cable for supplying an electric power and transmitting a signal is connected with the photo interrupter. The cable moves together with the moving stage and bends whenever the moving stage moves. Thus, the cable may be cut off.

Further, the moving stage is moved upward by the autosampler and thus the container on the moving stage is made to be closer to the capillary anode electrode. At this time, the capillary electrode comes close to the photo interrupter on the moving stage. For that reason, failure of the photo interrupter may be caused by an electric discharge from the capillary electrode at the time of electrophoresis.

The sample plate identification mechanism of the embodiment is formed so as to solve such problems. The sample plate identification mechanism of the embodiment has one or plurality of detection plates 5017 provided on the side surface of the sample plate assembly 501 and one or plurality of photo interrupters 311 provided on a fixed portion 310 of the capillary electrophoresis apparatus.

In the sample plate identification mechanism of the embodiment, the photo interrupter 311 is not provided on the moving stage 302. Thus, even when liquid falls on the moving stage 302, an electric failure is not caused. Therefore, this is very useful for the capillary electrophoresis apparatus in which the operator places containers containing liquids on the moving stage.

Further, the photo interrupter 311 is mounted on the fixed portion 310. Thus, even when the moving stage 302 moves, the cable connected to the photo interrupter is not moved. Therefore, the cable is not cut off. According to the embodiment, the photo interrupter is disposed at the position away from the capillary electrode. Thus, the failure of the photo interrupter caused by the electric discharge from the capillary electrode can be avoided.

The method for using the sample plate identification mechanism of the embodiment will be described with reference to FIG. 5B. In order to identify the type of sample plate, it is necessary to move the moving stage 302 until the sample plate assembly 501 comes closer to the photo interrupter 311. That is, the moving stage 302 is moved so that the detection plate 5017 provided in the sample plate assembly 501 is engaged with the photo interrupter 311. The information obtained by the photo interrupter 311 is stored into a memory element on a control board of the apparatus or on the control computer of the apparatus.

According to the embodiment, it is not necessary to form the photo interrupter on the upper surface of the moving stage 302. Therefore, the upper surface of the moving stage 302 can be formed to have a flat one without holes. When liquid falls on the moving stage 302, it may be simply wiped off. A frame may be provided on the edge of the upper surface of the moving stage 302. In this case, the liquid fallen on the upper surface of the moving stage is prevented from falling below the moving stage. Therefore, the moving stage which has high operational reliability and is hygienic can be formed.

In the embodiment, the moving stage 302 is moved and the detection plate 5017 of the sample plate assembly 501 is engaged with the photo interrupter 311. Therefore, the direction in which the detection plate 5017 proceeds into the photo interrupter 311 is a horizontal direction. When the frame is formed on the edge of the upper surface of the moving stage 302, it is necessary to delete the frame at the portion where the detection plate 5017 of the sample plate assembly 501 is disposed.

Figure 6:
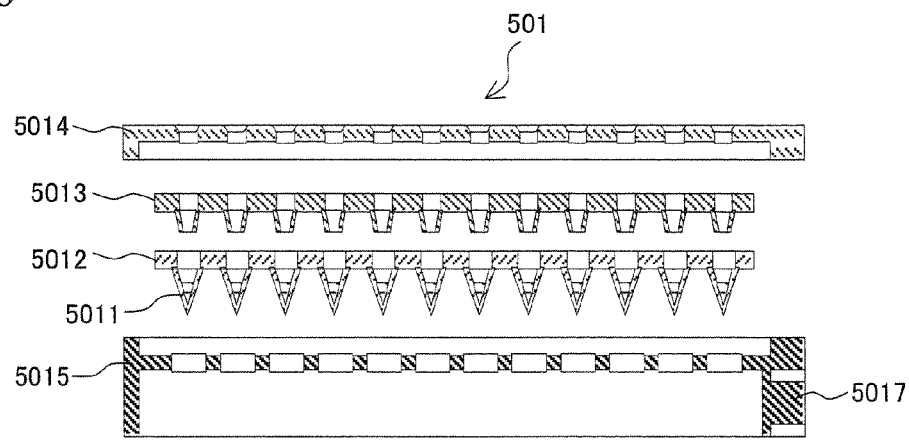
FIG. 6 is a diagram explaining an example of the structure of the sample plate assembly according to the invention.

As shown in FIG. 6, the sample plate assembly 501 of the embodiment has a structure in which the septa 5013 is attached to the sample plate 5012 containing the sample 5011, which is sandwiched between an adapter 5015 and a clip 5014. In the sample plate assembly 501 of the embodiment, the detection plate 5017 is provided on the side surface of the adapter 5015.

Figure 7:
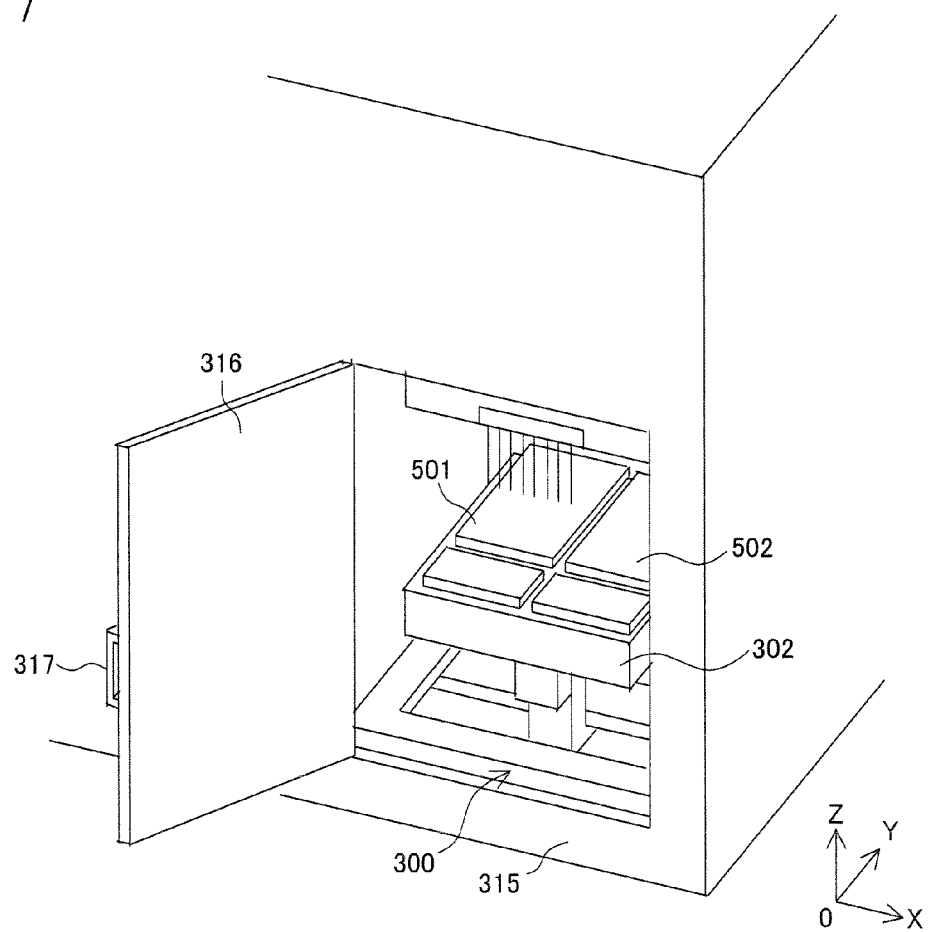
FIG. 7 is an explanatory diagram explaining an example of the operation of the sample plate identification mechanism of the autosampler according to the invention.

An example of the method for identifying the type of sample plate will be described with reference to FIG. 7. In the embodiment, recognition of the type of sample plate is not always performed. It is carried out when necessary. For example, it is performed when the sample plate assembly is disposed on the moving stage or when the sample plate assembly on the moving stage is replaced with another sample plate assembly. It is preferable that the type of sample plate is automatically recognized when the sample plate assembly is disposed on the moving stage or when the sample plate assembly on the moving stage is replaced.

The autosampler 300 of the embodiment is housed in a housing 315. A door 316 is provided on the housing 315. The sample plate assemblies 501 and 502 cannot be taken in and out without passing through the door 316. According to the embodiment, an opening-and-closing detection mechanism 317 which detects opening and closing of the door 316 is provided. The opening-and-closing detection mechanism 317 may be a limit switch or a photosensor. The opening-and-closing detection mechanism 317 may detect when the door 316 is opened or when it is closed. Further, the opening-and-closing detection mechanism 317 may detect both when the door 316 is opened and when it is closed.

A detection signal from the opening-and-closing detection mechanism 317 is transmitted to a control portion of the capillary electrophoresis apparatus and further transmitted to the autosampler 300. As a result, the moving stage 302 is moved. When the detection plate of the sample plate assembly is engaged with the photo interrupter, the type of sample plate is identified. According to the embodiment, the type of sample plate is automatically recognized when the sample plate assembly is disposed on the moving stage or when the sample plate assembly on the moving stage is replaced.

When the capillary electrophoresis apparatus is powered off, the opening-and-closing detection mechanism does not operate. Therefore, in the case where the capillary electrophoresis apparatus is powered off, even when the door 316 is opened, and the sample plate assemblies 501 and 502 are disposed on the moving stage 302 or the sample plate assemblies 501 and 502 on the moving stage 302 are replaced, the type of sample plate is not recognized.

The embodiment has a structure in which an operation for identifying the type of sample plate is performed when the power supply of the capillary electrophoresis apparatus is turned on. Therefore, when the capillary electrophoresis apparatus is powered off, the sample plate assembly may be disposed on the moving stage or the sample plate assembly on the moving stage may be replaced.

Although the case has been described in which the detection plate and the photo interrupter are used as the sample plate identification mechanism, the other structures can be used as the sample plate identification mechanism. Here, an example using Radio Frequency Identification (RFID) technology will be described.

An RF tag (IC chip) which can transmit and receive radiofrequency waves is provided on the side surface of the sample plate assembly 501. An RF reader writer (transmitting and receiving antenna) is provided in the fixed portion 310 of the capillary electrophoresis apparatus. In order to identify the type of sample plate, the moving stage 302 is moved until the RF tag comes closer to the RF reader writer. In other words, the moving stage 302 is moved until the RF tag can be read by the RF reader writer. Incidentally, when the sizes of the RF tag and the RF reader writer are increased, the RF tag can be read by the RF reader writer even if the RF tag is away from the RF reader writer. In this case, the type of sample plate on the moving stage can always be read. For that matter, the RF tag is mounted on any of the parts which constitute the sample plate assembly 501. The RF tag may be mounted on the adapter 5015 and it may be mounted on the sample plate 5012. As described in JP-A-2003-344357, barcodes may be mounted on the parts which constitute the sample plate assembly 501 and a bar code reader may be mounted on the fixed portion 310.

When the capillary electrode is taken out from the container, the moving stage on which the container is placed is lowered. At this time, the septa are lifted up by a frictional force between the capillary electrode and the hole of the septa of the container. As a result, the septa are deformed or the sample plate assembly may be lifted together with the septa.

The use of a stripper plate for pressing the septa on the container is described in JP-A-2001-324474. The stripper plate prevents the septa from being lifted and the capillary electrode can be detached from the septa.

However, when the stripper plate is used, a space where the stripper plate is disposed is needed between the bottom of the capillary electrode and the septa. Thus, it is necessary to make the length of the capillary electrode longer so as to provide a space required for the disposition of the stripper plate. On the other hand, it is preferable that the capillary electrode is short from the viewpoint of the separation performance of electrophoresis. This is because the capillary electrode is disposed in the outside of the oven and thus it is easily influenced by outside air temperatures. When the temperature of the capillary electrode is changed due to outside air temperatures, variation in the separation performance is caused.

The mechanism in which the sample plate assembly is held by the gripper is disclosed in JP-A-2003-344357. The gripper holds the sample plate assembly directly, thereby allowing the sample plate assembly to be held. However, an actuator which drives the gripper and a motor are needed, the apparatus is complicated, and the number of parts is increased. Further, when the moving stage moves, the gripper also moves three-dimensionally. Therefore, a wiring of the actuator moves and thus the risk of disconnection increases.

According to the invention, a mechanism which fixes the sample plate assembly to the moving stage of the autosampler is provided as described hereinafter.

Figure 8:
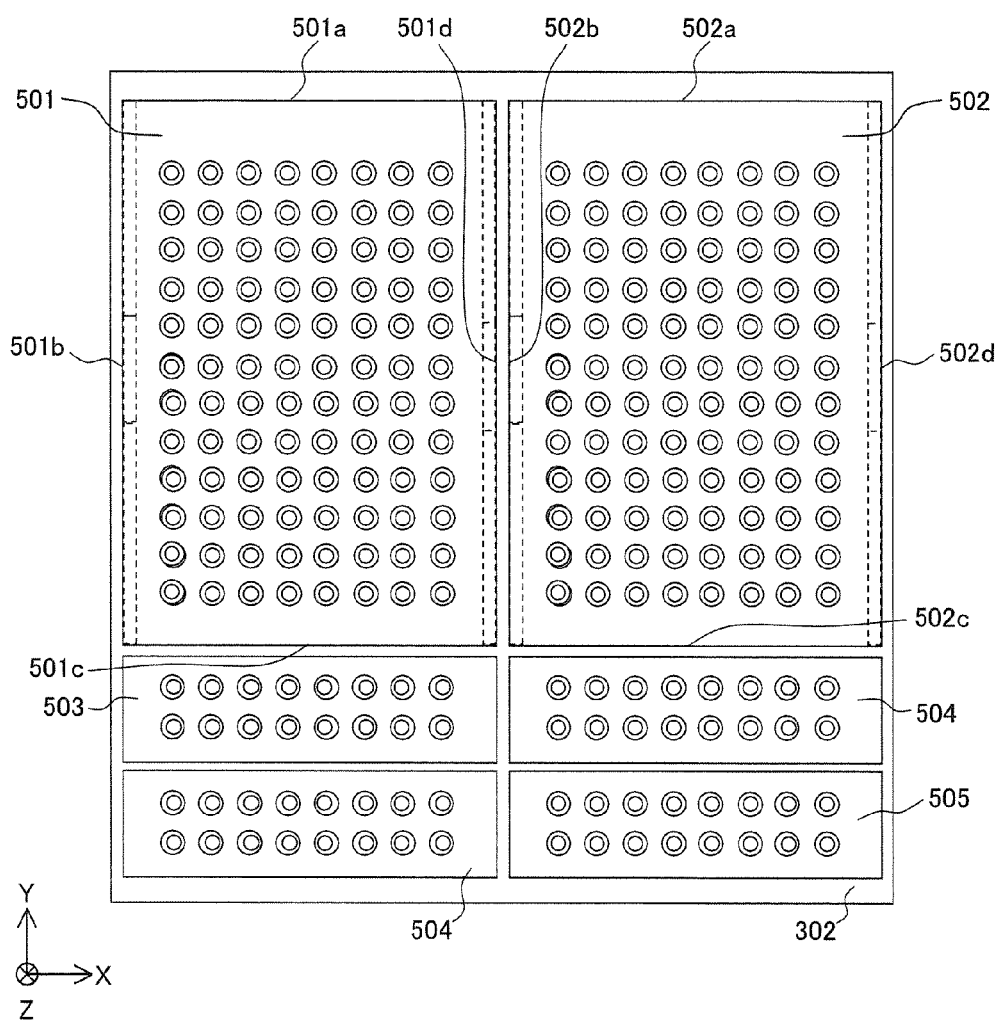
FIG. 8 is an explanatory diagram explaining an installed position of the fixation mechanism of the sample plate assembly provided on the moving stage of the autosampler according to the invention.

FIG. 8 illustrates a plane configuration of the sample plate assemblies 501 and 502 disposed on the moving stage 302, the buffer container 503, the cleaning container 504, and the waste liquid container 505. Here, a position of the fixation mechanism which fixes the sample plate assemblies 501 and 502 on the moving stage is considered. As shown in the drawings, the first sample plate assembly 501 has four side surfaces 501a to 501d and the second sample plate assembly 502 has four side surfaces 502a to 502d. The fixation mechanism is provided in each of the sample plate assemblies 501 and 502. The two sample plate assemblies are the same and one of the sample plate assemblies 501 and 502, the sample plate assembly 501, is considered. It is considered that any of the four side surfaces 501a, 501b, 501c, and 501d, the upper surface, and the bottom is preferable to provide the fixation mechanism of the sample plate assembly 501. The sample plate identification mechanism which identifies the type of sample plate is provided on the side surface 501a of the sample plate assembly. In the above-described example, the sample plate identification mechanism is the detection plate or the RF tag. Therefore, the fixation mechanism cannot be provided on the side surface 501a of the sample plate assembly. The inside side surface 501d of the sample plate assembly is close to the second sample plate assembly 502. Therefore, there is no enough space to provide the fixation mechanism on the side surface 501d of the sample plate assembly. The side surface 501c of the sample plate assembly is close to the buffer container 503. There is no enough space to provide the fixation mechanism on the side surface 501c of the sample plate assembly.

The upper surface of the sample plate assembly 501 is considered. The capillary electrode is disposed above the sample plate assembly 501. Therefore, when the fixation mechanism is provided on the upper surface of the sample plate assembly 501, the capillary electrode may interfere at the time of operating the fixation mechanism. For example, the fixation mechanism having a structure such as a lid is assumed as the fixation mechanism. When the lid is opened and closed, the lid may collide with the capillary electrode. When the lid collides with the capillary electrode, the lid or the capillary electrode is damaged. On the other hand, when the fixation mechanism is provided on the bottom surface of the sample plate assembly 501, the operation is complicated.

In the embodiment, the fixation mechanism is provided on the outside side surface 501b of the first sample plate assembly 501. Similarly, the fixation mechanism is provided on the outside side surface 502d of the second sample plate assembly 502. The position to provide the fixation mechanism is determined in the manner as described above. In the embodiment, the case where a pair of the sample plate assemblies 501 and 502 are arranged and disposed on the moving stage has been considered. The same holds for the case where a plurality of pairs of the sample plate assemblies are disposed. Subsequently, the structure of the fixation mechanism will be considered. The fixation mechanism has the following conditions:

(1) it is necessary to position the sample plate assembly on the moving stage with a high degree of accuracy. Thus, a mechanism which controls the movement of the sample plate assembly in the back-and-forth direction (Y-axis direction) and the right-and-left direction (X-axis direction) is needed; and (2) it is necessary that a load in the back-and-forth direction (Y-axis direction) and the right-and-left direction (X-axis direction) is not applied to the sample plate assembly when the sample plate assembly is attached to the moving stage and when it is detached from the moving stage. According to the invention, a belt driving which can speed up the transport is employed as a drive mechanism of the autosampler. However, the belt driving is easily influenced by loads and vibrations from the outside. Particularly, when the power supply is turned off, the moving stage is easily displaced by loads from the outside. The belt driving can be employed by providing a structure in which loads are not generated when the fixation mechanism is operated.

Figure 9A:
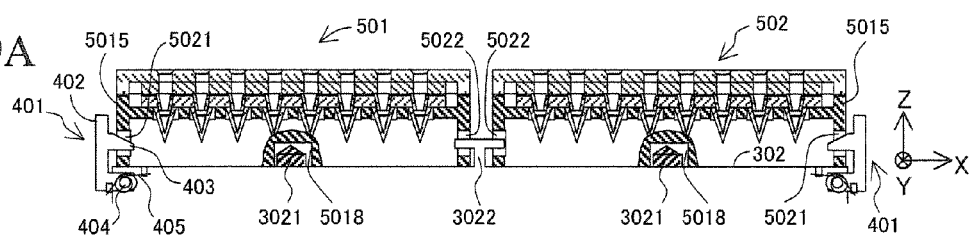
FIGS. 9A-9F are explanatory diagrams explaining the structure and operation of a first example of the fixation mechanism of the sample plate assembly provided on the moving stage of the autosampler according to the invention.

The first example of the fixation mechanism of the sample plate assembly provided on the moving stage of the invention will be described with reference to FIG. 9A. FIG. 9A shows a cross section structure of the moving stage 302 and the sample plate assemblies 501 and 502 which are disposed thereon.

According to the embodiment, movable hooks 401 are provided at both ends of the moving stage 302 and a fixed hook 3022 is provided in the center of the moving stage 302. Further, convex portions 3021 for positioning are provided on the moving stage. On the other hand, a hole 5021 is provided on the outside side surface of the sample plate assembly 501 and a hole 5022 is provided on the inside side surface of the sample plate assembly 501. Further, concave portions 5018 for positioning are provided on the bottom surface of the sample plate assembly 501. The position of the convex portions 3021 for positioning and the concave portions 5018 for positioning will be described with reference to FIG. 12.

Incidentally, the sample plate assemblies 501 and 502 may have the same structure as the sample plate assembly described with reference to FIG. 6. In this case, the holes 5021 and 5022 of the side surface of the sample plate assembly 501 are provided on the side surface of the adapter 5015. The concave portions 5018 for positioning of the bottom surface of the sample plate assembly 501 are provided on the bottom surface of the adapter 5015.

The movable hooks 401 provided at both ends of the moving stage 302 have the same structure. Here, the movable hook 401 on the left side of the moving stage 302 will be described. The movable hook 401 is disposed on the outside of the sample plate assembly 501 and has a lever portion 402 and a claw 403 which is inwardly extended. The claw 403 is formed so as to be engaged with the hole 5021 of the outside side surface of the sample plate assembly 501. The fixed hook 3022 has a claw which is outwardly extended to both sides. The claw of the fixed hook 3022 is formed so as to be engaged with the hole 5022 of the inside side surface of the sample plate assembly 501. Further, the convex portions 3021 on the moving stage 302 are formed so as to be engaged with the concave portions 5018 of the bottom surface of the sample plate assembly 501. Thus, the sample plate assembly 501 can be accurately positioned on a predetermined position on the moving stage 302 by engaging the convex portions 3021 on the moving stage 302 with the concave portions 5018 of the bottom surface of the sample plate assembly 501.

The movable hook 401 is rotatable about a shaft 404. The shaft 404 is disposed along the Y-axis direction (perpendicular to the plane of paper). Therefore, the movable hook 401 rotates along a vertical plane. A torsion spring 405 is wound around the shaft 404. One end of the torsion spring 405 is mounted on the movable hook 401 and the other end is mounted on the bottom surface of the moving stage 302. The torsion spring 405 exerts a force in a closed direction on the movable hook 401.

Figure 9B:
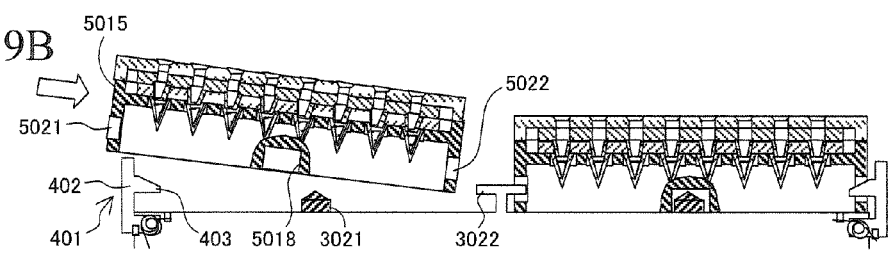
Figure 9C:
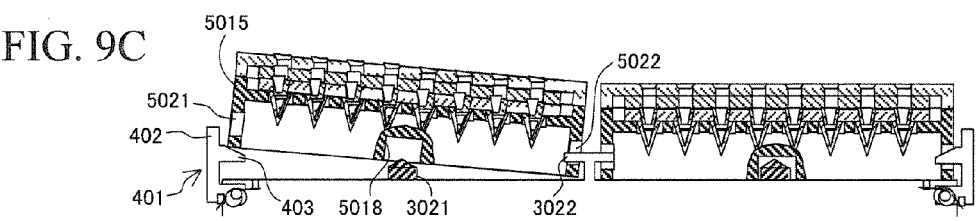

A method for fixing the sample plate assembly of the embodiment on the moving stage will be described with reference to FIGS. 9B to 9F. As shown in FIG. 9B, first, the sample plate assembly 501 is disposed above the moving stage 302, being inclined so that the outer edge is elevated and the inner edge is lowered in position. As shown in FIG. 9C, the hole 5022 of the inside side surface of the sample plate assembly 501 is engaged with the claw of the fixed hook 3022.

Figure 9D:
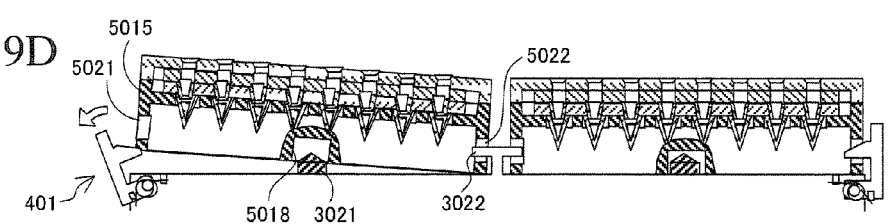
Figure 9E:
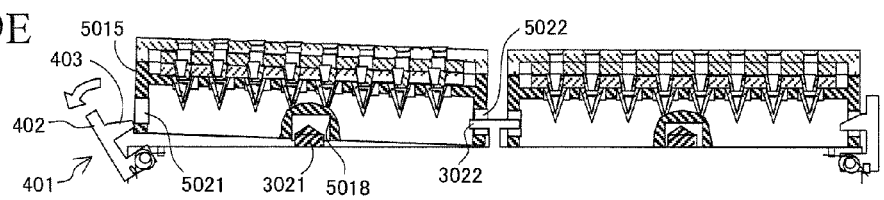
Figure 9F:
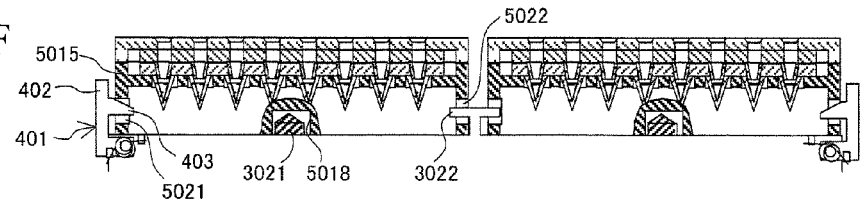

As shown in FIG. 9D, the movable hook 401 (in FIG. 9D) is rotated in the counterclockwise direction by resisting a biasing force of the torsion spring 405. As shown in FIG. 9E, the outer edge of the sample plate assembly is pushed downwardly and the concave portions 5018 of the bottom surface of the sample plate assembly 501 are engaged with the convex portions 3021 on the moving stage 302. Thus, the hole 5022 of the inside side surface of the sample plate assembly 501 is engaged with the claw of the fixed hook 3022 and the concave portions 5018 of the bottom surface of the sample plate assembly 501 are engaged with the convex portions 3021 on the moving stage 302. Finally, the sample plate assembly 501 in a horizontal state is disposed on the moving stage 302 as shown in FIG. 9F. The movable hook 401 is rotated in the clockwise direction along a vertical plane (in FIG. 9F) by using the biasing force of the torsion spring 405. As a result, the claw 403 of the movable hook 401 is engaged with the hole 5021 of the outside side surface of the sample plate assembly 501.

Figure 10A:
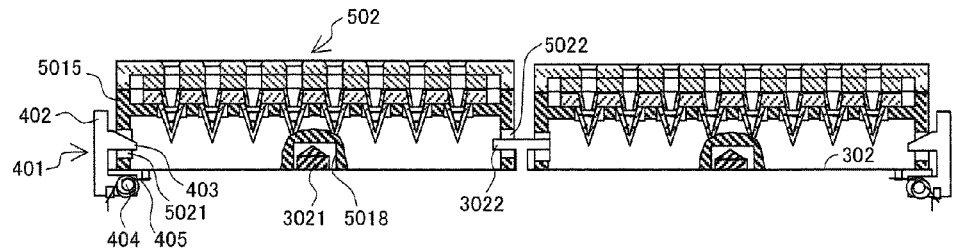
FIGS. 10A-10D are explanatory diagrams explaining the operation of the first example of the fixation mechanism of the sample plate assembly provided on the moving stage of the autosampler according to the invention.
Figure 10B:
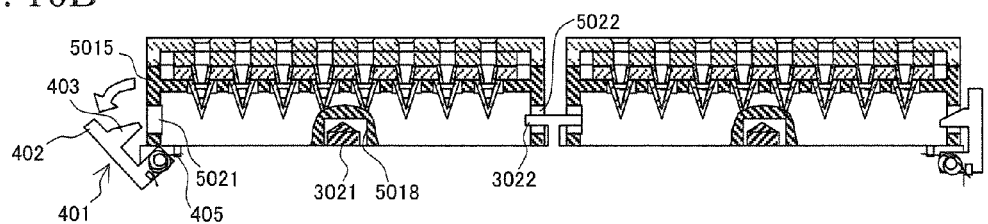
Figure 10C:
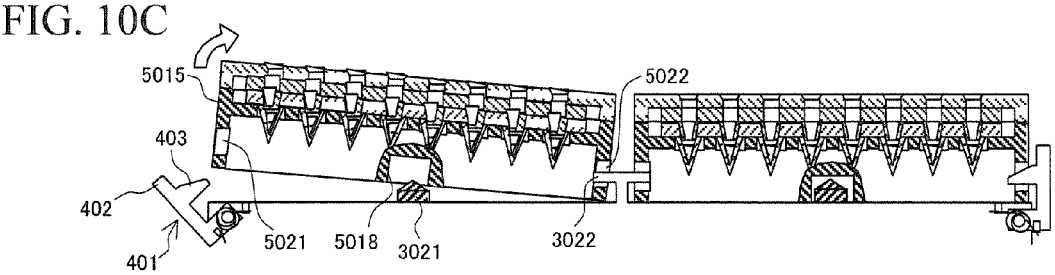
Figure 10D:
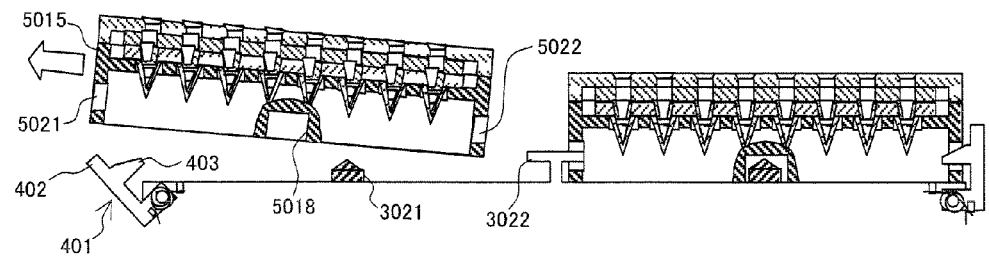

A method for detaching the sample plate assembly of the embodiment from the moving stage will be described with reference to FIGS. 10A to 10D. FIG. 10A is the same as FIG. 9A. The sample plate assembly 501 is mounted on the moving stage 302 and fixed by the fixing apparatus. As shown in FIG. 10B, the movable hook 401 is rotated in the counterclockwise direction along a vertical plane by resisting the biasing force of the torsion spring 405. As a result, the claw 403 of the movable hook 401 is detached from the hole 5021 of the outside side surface of the sample plate assembly 501. As shown in FIG. 10C, the sample plate assembly 501 is inclined by lifting the outer edge of the sample plate assembly 501. As a result, the concave portions 5018 of the bottom surface of the sample plate assembly 501 are detached from the convex portions 3021 on the moving stage 302. At this time, the hole 5022 of the inside side surface of the sample plate assembly 501 is engaged with the fixed hook 3022. Finally, the sample plate assembly 501 is lifted overall as shown in FIG. 10D. As a result, the hole 5022 of the inside side surface of the sample plate assembly 501 is detached from the claw of the fixed hook 3022.

A direction for lifting the sample plate assembly 501 of FIG. 10C is an opposite direction to the direction for rotating the movable hook 401 of FIG. 10B. Therefore, the operation of FIG. 10B is performed by one hand and the operation of FIG. 10C is performed by the other hand. Finally, the operation for lifting the sample plate assembly 501 may be carried out by both hands.

In the fixing apparatus of the embodiment, when the sample plate assembly 501 is mounted on the moving stage 302 and removed therefrom, a load in the up-and-down direction is applied to the moving stage 302, however, a load in back-and-forth and right-and-left directions is not applied thereto. Therefore, in the embodiment, the belt driving which can speed up the transport is employed as the drive mechanism of the autosampler.

Figure 11A:
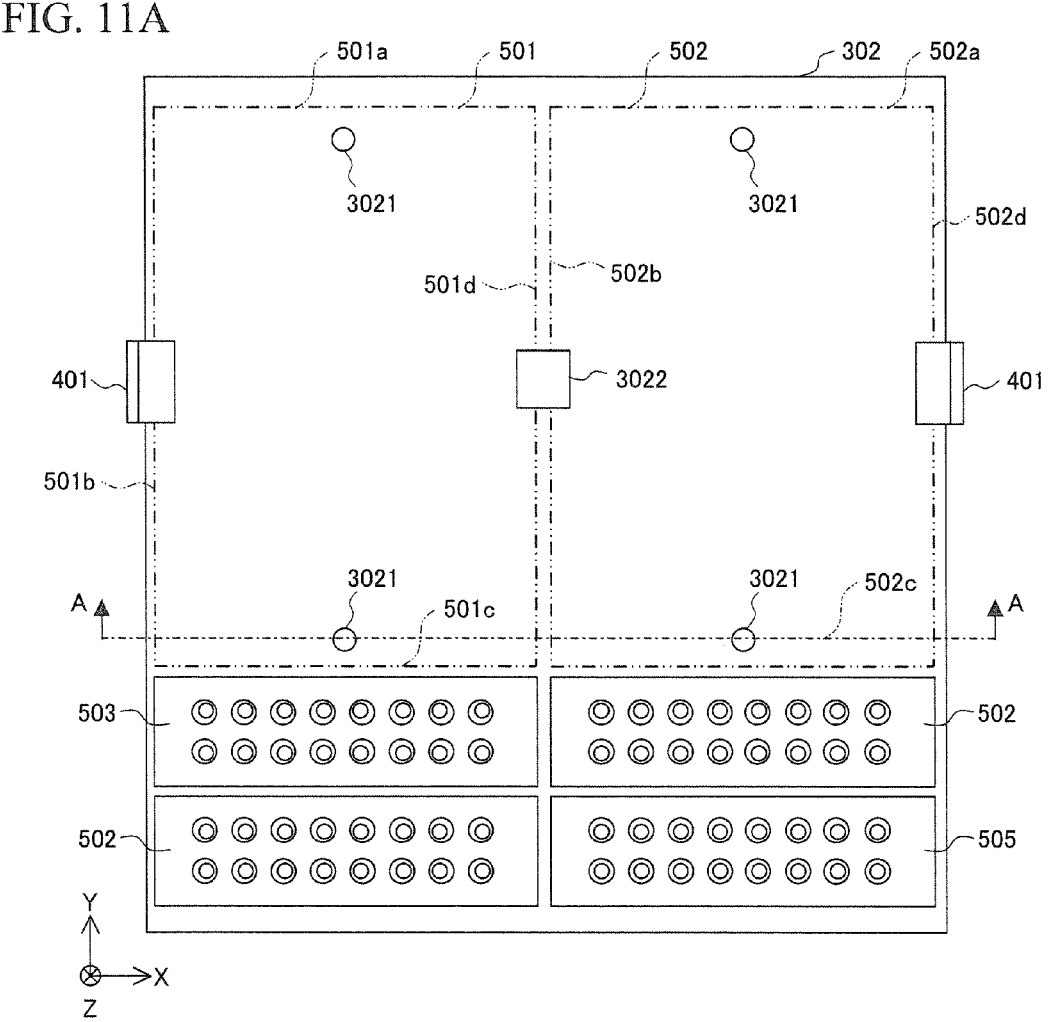
FIGS. 11A and 11B are explanatory diagrams explaining an example of the fixation mechanism provided on the moving stage of the autosampler according to the invention.
Figure 11B:
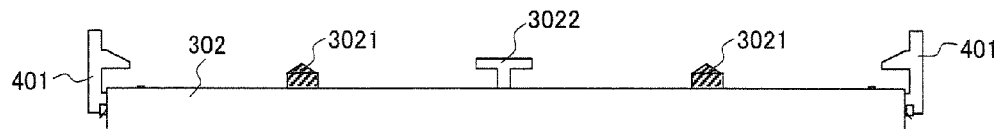

A structure of the upper surface of the moving stage 302 of the embodiment will be described with reference to FIGS. 11A and 11B. FIG. 11A shows an upper surface structure of the moving stage 302 according to the invention. FIG. 11B shows a cross section structure of the moving stage 302. Dashed-two dotted lines of FIG. 11A indicate positions of the sample plate assemblies 501 and 502. As shown in the drawings, the convex portions 3021 are provided on the upper surface of the moving stage 302. The convex portions 3021 are close to the side surfaces 501a and 501c as well as the side surfaces 502a and 502c of the sample plate assemblies 501 and 502 and disposed inside from the side surfaces 501a and 501c as well as the side surfaces 502a and 502c. The movable hook 401 and the fixed hook 3022 are disposed nearly in the center in a longitudinal direction of the sample plate assembly. In other words, the movable hooks 401 are disposed nearly in the center in a longitudinal direction (Y-axis direction) along the outside side surfaces 501b and 502d of the sample plate assemblies 501 and 502. The fixed hook 3022 is disposed nearly in the center in a longitudinal direction (Y-axis direction) along the inside side surfaces 501d and 502b of the sample plate assemblies 501 and 502. The claw of the movable hook 401 has a predetermined size. Similarly, the claw of the fixed hook 3022 has a predetermined size.

Figure 12A:
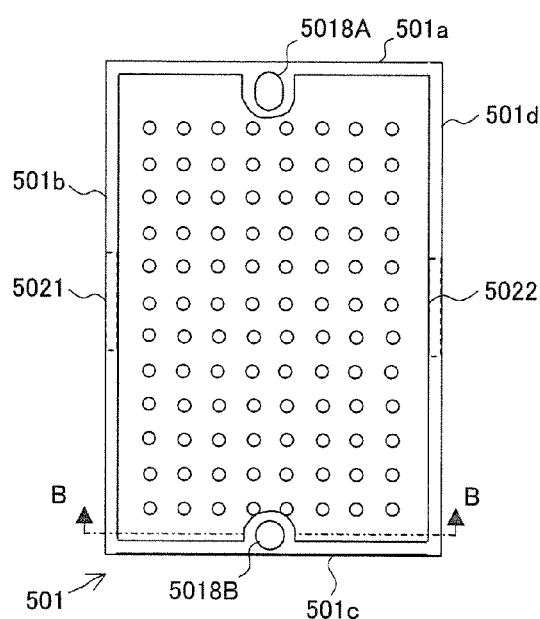
FIGS. 12A-12E are explanatory diagrams explaining an example of the fixation mechanism provided on the sample plate assembly according to the invention.
Figure 12B:
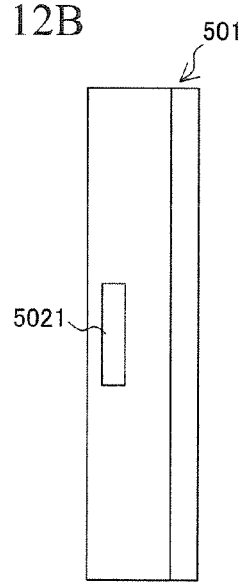
Figure 12C:
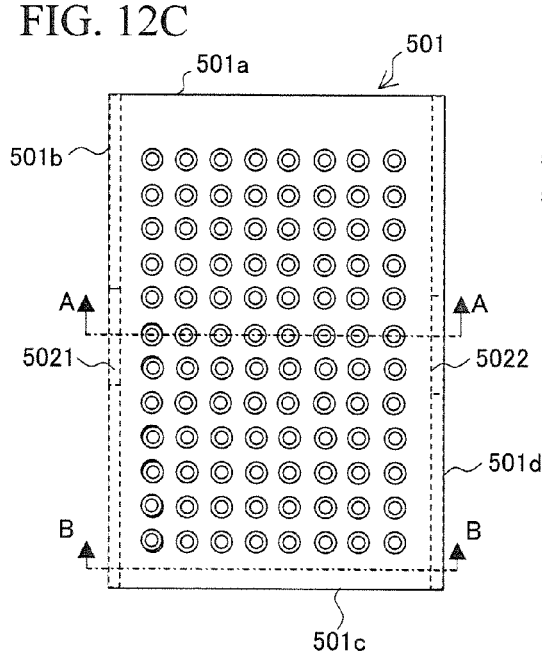
Figure 12D:
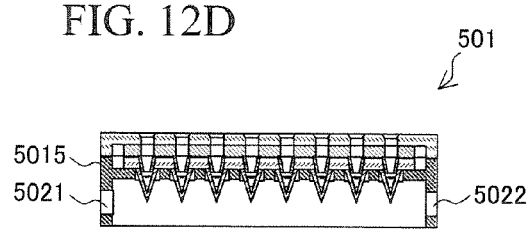
Figure 12E:
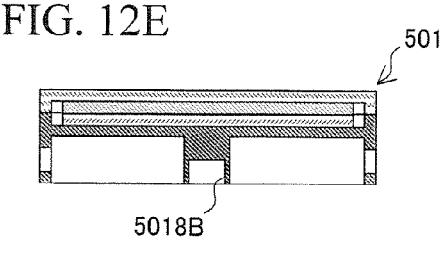

An example of the sample plate assembly of the embodiment will be illustrated with reference to FIGS. 12A to 12E. FIG. 12A shows a bottom surface structure of the sample plate assembly of the embodiment. FIG. 12B shows a side surface structure of the sample plate assembly of the embodiment. FIG. 12C shows an upper surface structure of the sample plate assembly of the embodiment. FIG. 12D shows a cross section structure in which the sample plate assembly of FIG. 12C is cut along a line A-A. FIG. 12E shows a cross section structure in which the sample plate assembly of FIG. 12C is cut along a line B-B.

As shown in FIGS. 12A and 12E, concave portions 5018A and 5018B are provided on the bottom surface of the sample plate assembly 501 of the embodiment. The concave portion 5018A is close to the side surface 501a and disposed inside from the side surface 501a. The concave portion 5018B is close to the side surface 501c and disposed inside from the side surface 501c. The concave portions 5018A and 5018B are disposed at the positions corresponding to the convex portions 3021 of the upper surface of the moving stage shown in FIG. 11A. The concave portion 5018A provided close to the side surface 501a has an elongate hole while the concave portion 5018B provided close to the side surface 501c has a round hole.

As shown in FIGS. 12B and 12D, the holes 5021 and 5022 are provided on the side surface of the sample plate assembly of the embodiment. The holes 5021 and 5022 are disposed nearly in the center in a longitudinal direction of the sample plate assembly 501. The holes 5021 and 5022 are disposed at the positions corresponding to the movable hook 401 and the fixed hook 3022 of the upper surface of the moving stage as shown in FIG. 11A. The holes have a predetermined size capable of receiving the claw of the movable hook 401 and the claw of the fixed hook 3022.

Figure 13A:
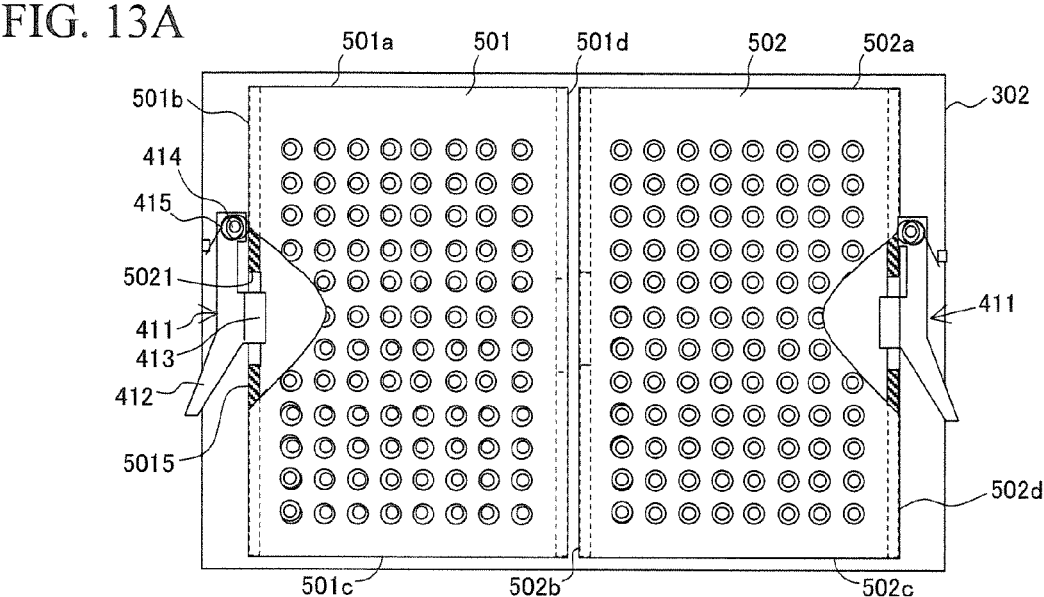
FIGS. 13A-13D are explanatory diagrams explaining a second example of the fixation mechanism of the sample plate assembly provided on the moving stage of the autosampler according to the invention.
Figure 13B:
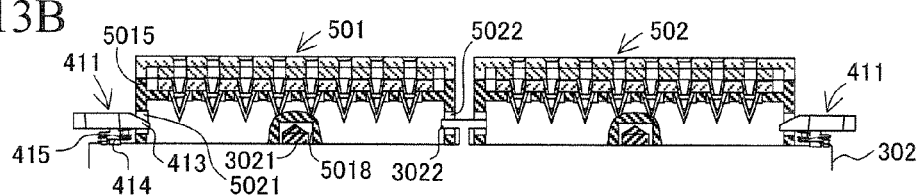

The second example of the fixation mechanism of the sample plate assembly provided on the moving stage of the invention will be described with reference to FIGS. 13A and 13B. According to the embodiment, movable hooks 411 are provided at both ends of the moving stage 302. The movable hooks 411 are disposed corresponding to the positions of the outside side surfaces 501b and 502d of the sample plate assemblies 501 and 502. The fixed hook 3022 is provided in the center of the moving stage 302. Further, convex portions 3021 for positioning are provided on the moving stage. On the other hand, the hole 5021 is provided on the outside side surface of the sample plate assembly 501 and the hole 5022 is provided on the inside side surface of the sample plate assembly 501. Further, the concave portions 5018 for positioning are provided on the bottom surface of the sample plate assembly 501. The position of the convex portions 3021 for positioning and the concave portions 5018 for positioning have been described with reference to FIG. 12.

Incidentally, the sample plate assemblies 501 and 502 may have the same structure as the sample plate assembly described with reference to FIG. 6. In this case, the holes 5021 and 5022 of the side surface of the sample plate assembly 501 are provided on the outside side surface of the adapter 5015. The concave portions 5018 for positioning of the bottom surface of the sample plate assembly 501 are provided on the bottom surface of the adapter 5015.

The movable hooks 411 provided at both ends of the moving stage 302 have the same structure. Here, the movable hook 411 on the left side of the moving stage 302 will be described. The movable hook 411 is disposed on the outside of the sample plate assembly 501 and has a lever portion 412 and a claw 413 which is inwardly extended. The claw 413 is formed so as to be engaged with the hole 5021 of the outside side surface of the sample plate assembly 501. The fixed hook 3022 has a claw which is outwardly extended to both sides. The claw of the fixed hook 3022 is formed so as to be engaged with the hole 5022 of the inside side surface of the sample plate assembly 501. Further, the convex portions 3021 on the moving stage 302 are formed so as to be engaged with the concave portions 5018 of the bottom surface of the sample plate assembly 501. Thus, the sample plate assembly 501 can be accurately positioned on a predetermined position on the moving stage 302 by engaging the convex portions 3021 on the moving stage 302 with the concave portions 5018 of the bottom surface of the sample plate assembly 501.

The movable hook 411 is rotatable about the shaft 414. The shaft 414 is disposed along the Z-axis direction (thickness direction of the sample plate assembly 501). Therefore, the movable hook 411 rotates along a horizontal plane. The torsion spring 415 is wound around the shaft 414. One end of the torsion spring 415 is mounted on the movable hook 411 and the other end is mounted on the bottom surface of the moving stage 302. The torsion spring 415 exerts the force in the closed direction, on the movable hook 411.

Figure 13C:
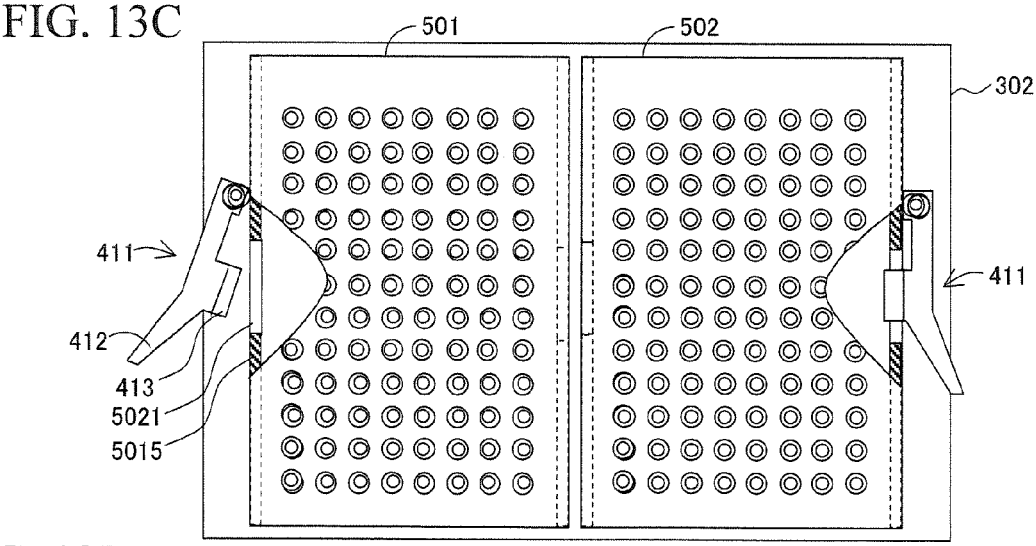
Figure 13D:
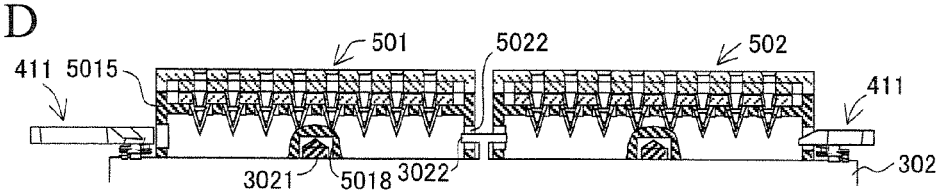

An operation of the fixing apparatus of the embodiment will be described with reference to FIGS. 13C and 13D. When the sample plate assembly is mounted or removed, the lever portion 412 of the movable hook 411 is rotated in the clockwise direction along a horizontal plane (in FIG. 13C) by resisting the biasing force of the torsion spring 415. As a result, the claw 413 of the movable hook 411 is detached from the hole 5021 provided on the outside side surface of the sample plate assembly 501. FIGS. 13C and 13D show a state in which the claw 413 of the movable hook 411 is thus detached from the hole 5021 of the outside side surface of the sample plate assembly 501. When the sample plate assembly 501 is fixed by the fixing apparatus, the movable hook 411 is made to rotate in the counterclockwise direction along a horizontal plane (in FIG. 13C) by using the biasing force of the torsion spring 415. As a result, the claw 413 of the movable hook 411 is engaged with the hole 5021 of the outside side surface of the sample plate assembly 501. According to the embodiment, the size of the hole 5021 provided on the outside side surface of the sample plate assembly 501 is larger than the size of the claw 413 of the movable hook 411. Thus, even if the claw 413 of the movable hook 411 draws an arc around the shaft 414, the claw of the movable hook 411 does not collide with the hole 5021 of the outside side surface of the sample plate assembly 501.

In the embodiment, the operation of rotating the movable hook is performed along a horizontal plane and the operation of removing the sample plate assembly is performed along the vertical plane. That is, both operating directions are perpendicular to each other. For that reason, the operation of rotating the movable hook and the operation of removing the sample plate assembly can be simultaneously performed with one hand, which is thus excellently convenient.

Figure 14A:
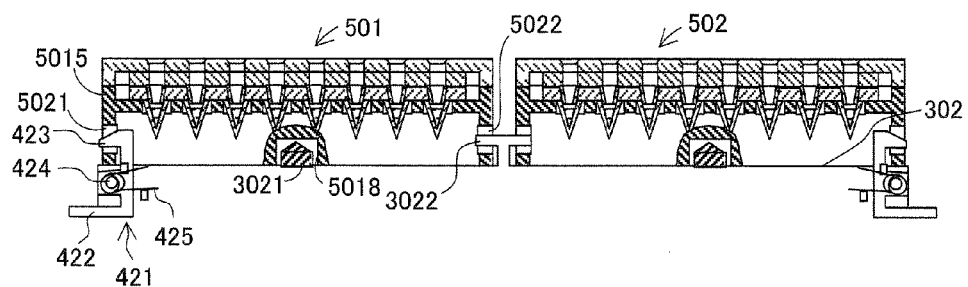
FIGS. 14A and 14B are explanatory diagrams explaining a third example of the fixation mechanism of the sample plate assembly provided on the moving stage of the autosampler according to the invention.
Figure 14B:
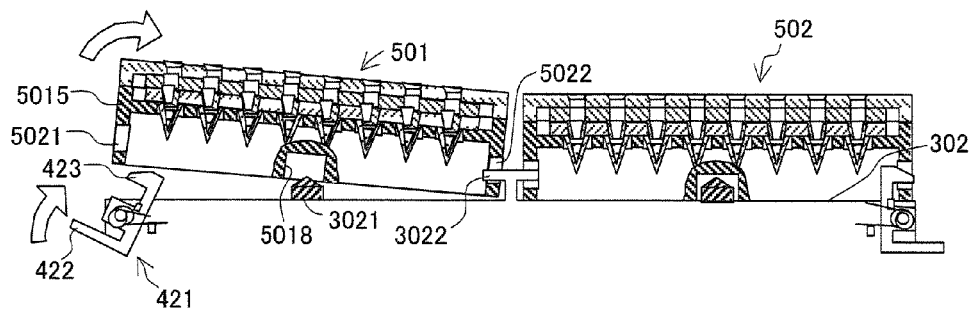

The third example of the fixation mechanism of the sample plate assembly provided on the moving stage of the invention will be described with reference to FIGS. 14A and 14B.

According to the embodiment, movable hooks 421 are provided at both ends of the moving stage 302 and the fixed hook 3022 is provided in the center of the moving stage 302. Further, the convex portions 3021 for positioning are provided on the moving stage. On the other hand, the hole 5021 is provided on the outside side surface of the sample plate assembly 501 and the hole 5022 is provided on the inside side surface of the sample plate assembly 501. Further, the concave portions 5018 for positioning are provided on the bottom surface of the sample plate assembly 501. The positions of the convex portions 3021 for positioning and the concave portions 5018 for positioning have been described with reference to FIG. 12.

Incidentally, the sample plate assemblies 501 and 502 may have the same structure as the sample plate assembly described with reference to FIG. 6. In this case, the holes 5021 and 5022 of the side surface of the sample plate assembly 501 are provided on the outside side surface of the adapter 5015. The concave portions 5018 for positioning of the bottom surface of the sample plate assembly 501 are provided on the bottom surface of the adapter 5015.

The movable hooks 421 provided at both ends of the moving stage 302 have the same structure. Here, the movable hook 421 on the left side of the moving stage 302 will be described. The movable hook 421 is disposed on the outside of the sample plate assembly 501 and has a lever portion 422 which is outwardly extended and a claw 423 which is outwardly extended. The claw 423 is formed so as to be engaged with the hole 5021 of the outside side surface of the sample plate assembly 501. The fixed hook 3022 has a claw which is outwardly extended to both sides. The claw of the fixed hook 3022 is formed so as to be engaged with the hole 5022 of the inside side surface of the sample plate assembly 501. Further, the convex portions 3021 on the moving stage 302 are formed so as to be engaged with the concave portions 5018 of the bottom surface of the sample plate assembly 501. Thus, the sample plate assembly 501 can be accurately positioned on a predetermined position on the moving stage 302 by engaging the convex portions 3021 on the moving stage 302 with the concave portions 5018 of the bottom surface of the sample plate assembly 501.

The movable hook 421 is rotatable about a shaft 424. The shaft 424 is disposed along the Y-axis direction (perpendicular to the plane of paper). Therefore, the hook 421 rotates along a vertical plane. A torsion spring 425 is wound around the shaft 424. One end of the torsion spring 425 is mounted on the movable hook 421 and the other end is mounted on the bottom surface of the moving stage 302. The torsion spring 425 exerts a force in a closed direction, on the movable hook 421.

The operation of the fixing apparatus of the embodiment will be described. When the sample plate assembly is removed, the movable hook 421 is rotated in the clockwise direction along a horizontal plane (in FIG. 14A) by resisting the biasing force of the torsion spring 425. As a result, the claw of the movable hook 421 is detached from the hole 5021 of the outside side surface of the sample plate assembly 501. FIG. 14B shows a state in which the claw 423 of the movable hook 421 is thus detached from the hole 5021 of the outside side surface of the sample plate assembly 501. Then, the sample plate assembly 501 is inclined by lifting the outer edge of the sample plate assembly 501. As a result, the concave portions 5018 of the bottom surface of the sample plate assembly 501 are detached from the convex portions 3021 on the moving stage. Finally, the sample plate assembly 501 is lifted overall. As a result, the hole 5022 of the inside side surface of the sample plate assembly 501 is detached from the claw of the fixed hook 3022. When the sample plate assembly is mounted, a reverse operation may be performed.

In the embodiment, the operation of rotating the movable hook is performed along a vertical plane and the operation of removing the sample plate assembly is performed along the vertical plane. That is, both operating directions are the same. For that reason, the operation of rotating the movable hook and the operation of removing the sample plate assembly can be simultaneously performed with one hand, which is thus excellently convenient.

Figure 15A:
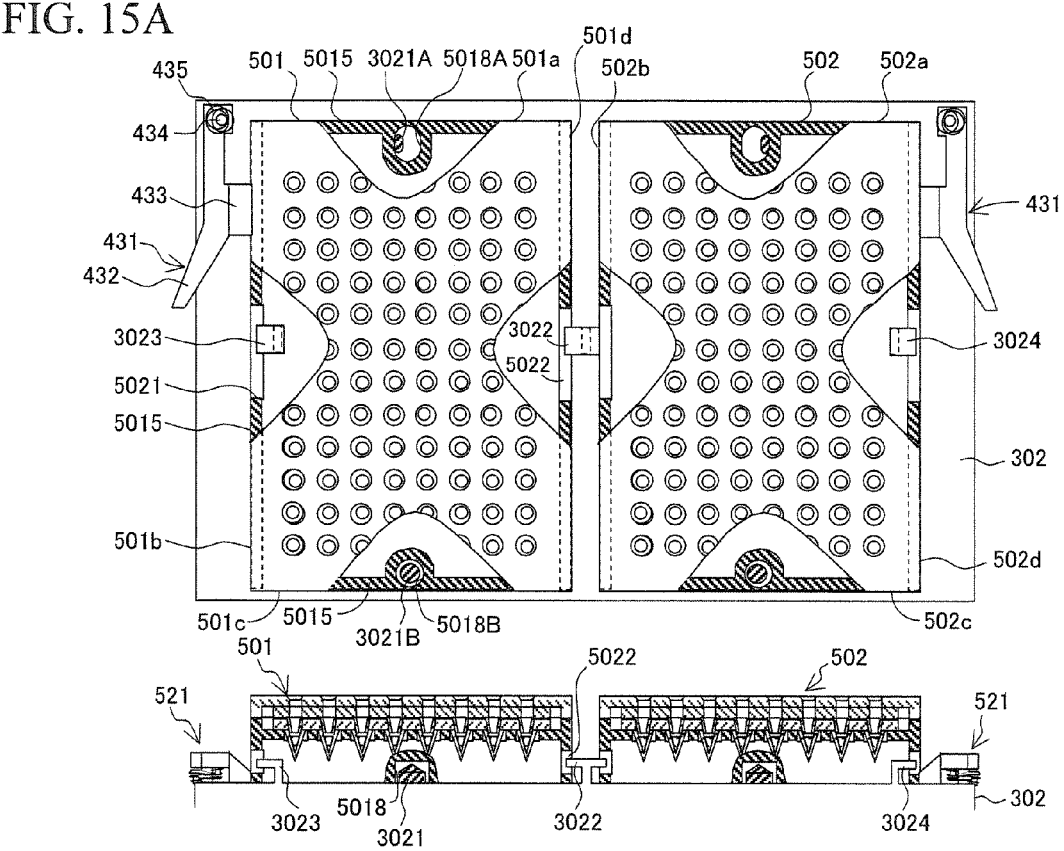
FIGS. 15A and 15B are explanatory diagrams explaining a fourth example of the fixation mechanism of the sample plate assembly provided on the moving stage of the autosampler according to the invention.

The fourth example of the fixation mechanism of the sample plate assembly provided on the moving stage of the invention will be described with reference to FIGS. 15A, 15B, and 15C.

According to the embodiment, movable hooks 431 are provided at both ends of the moving stage 302. The movable hooks 431 are disposed corresponding to the positions of the outside side surfaces 501b and 502d of the sample plate assemblies 501 and 502. The movable hooks 431 may be provided close to one of the side surfaces 501a of the sample plate assembly 501.

The fixed hooks 3022, 3023, and 3024 are arranged and provided in the center of the moving stage 302. The fixed hook 3022 is disposed at the position corresponding to the inside side surfaces 501d and 502b of the sample plate assemblies 501 and 502. Fixed hooks 3023 and 3024 are disposed at the position corresponding to the outside side surfaces 501b and 502d of the sample plate assemblies 501 and 502.

The hole 5021 is provided on the outside side surface of the sample plate assembly 501 and the hole 5022 is provided on the inside side surface of the sample plate assembly 501. The fixed hook 3023 is engaged with the hole 5021 of the outside side surface of the sample plate assembly 501. The fixed hook 3022 is engaged with the hole 5022 of the inside side surface of the sample plate assembly 501. The same holds for the second sample plate assembly 502.

Further, the convex portions 3021A and 3021B for positioning are provided on the moving stage. The convex portions 3021A and 3021B for positioning are disposed inside the inside side surfaces 501a and 501c of the first sample plate assembly 501. On the other hand, concave portions 5018A and 5018B for positioning are provided on the bottom surface of the first sample plate assembly 501.

The convex portions 3021A and 3021B for positioning on the moving stage are engaged with the concave portions 5018A and 5018B for positioning on the bottom surface of the sample plate assembly 501, respectively. The same holds both for the concave portions provided on the bottom surface of the second sample plate assembly 502 and for the convex portions for positioning provided on the moving stage which correspond to the concave portions.

In passing, the sample plate assemblies 501 and 502 may have the same structure as the sample plate assembly described with reference to FIG. 6. In this case, the holes 5021 and 5022 of the side surface of the sample plate assembly 501 are provided on the outside side surface of the adapter 5015. The concave portions 5018A and 5018B for positioning of the bottom surface of the sample plate assembly 501 is provided on the bottom surface of the adapter 5015. The same holds for the holes of the side surface of the sample plate assembly 502 and for the concave portions for positioning on the bottom surface.

The movable hooks 431 provided at both ends of the moving stage 302 have the same structure. Here, the movable hook 431 on the left side of the moving stage 302 will be described. The movable hook 431 is disposed on the outside of the sample plate assembly 501 and has a lever portion 432 and a pressing portion 433 which is inwardly extended. The pressing portion 433 is formed so as to press the outside side surface of the sample plate assembly 501.

The movable hook 431 is rotatable about a shaft 434. The shaft 434 is disposed along the Z-axis direction (thickness direction of the sample plate assembly 501). Therefore, the movable hook 431 rotates along the horizontal plane. A torsion spring 435 is wound around the shaft 434. One end of the torsion spring 435 is mounted on the movable hook 431 and the other end is mounted on the bottom surface of the moving stage 302. The torsion spring 425 exerts a force which makes a movable lever rotate in the counterclockwise direction along a horizontal plane (in FIG. 15A), on the movable lever.

Hereinafter, the first sample plate assembly 501 of the two sample plate assemblies 501 and 502 will described.

In the embodiment, the size of the hole 5021 of the outside side surface of the sample plate assembly 501 included in the first sample plate assembly 501 is sufficiently larger than the size of the claw of the fixed hook 3023. The size of the hole 5022 of the inside side surface of the sample plate assembly 501 is sufficiently larger than the size of the claw of the fixed hook 3022 in the center.

The size of the inner diameter of the concave portions 5018A and 5018B of the bottom surface of the sample plate assembly 501 is larger than the outer diameter of the convex portions 3021A and 3021B on the moving stage. A gap between the first concave portion 5018A (concave portion on the upper side in FIG. 15A) of the bottom surface of the sample plate assembly 501 and the first convex portion 3021A on the moving stage is larger than a gap between the second concave portion 5018B (concave portion on the lower side in FIG. 15A) and the second convex portion 3021B on the moving stage. The first concave portion 5018A may have an elongate hole in an elliptic shape. The cross section of the first convex portion 3021A on the moving stage may have an elliptic shape.

In the embodiment, there is a gap between an engaging portion formed on the moving stage and an engaging portion formed in the sample plate assembly 501. Thus, the sample plate assembly 501 is slightly movable on the moving stage 302. As for the gap between the engaging portion formed on the moving stage and the engaging portion formed in the sample plate assembly 501, the smallest gap is a gap between the second concave portion 5018B of the bottom surface of the sample plate assembly 501 and the second convex portion 3021B on the moving stage. Therefore, the sample plate assembly 501 on the moving stage 302 is rotatable around the second convex portion 3021B provided on the moving stage 302 at a slight rotation angle.

As shown in the drawings, the pressing portion 433 of the movable hook 431 presses the outside side surface of the sample plate assembly 501. Therefore, the sample plate assembly receives a pressure in the X-axis direction from the movable hook 431. Thus, the sample plate assembly on the moving stage rotates until the inside surface of the first concave portion 5018A of the bottom surface of the sample plate assembly 501 abuts on the first convex portion 3021A on the moving stage.

Even if the pressing force from the movable hook 431 is applied to the sample plate assembly, it is held in the condition when it cannot move any further.

An operation of the fixing apparatus of the embodiment will be described. When the sample plate assembly is removed, the lever portion 432 of the movable hook 431 is made to rotate in the clockwise direction along a horizontal plane (in FIG. 15A) by resisting the biasing force of the torsion spring 435. As a result, the pressing portion 433 of the movable hook 431 is separated from the outside side surface of the sample plate assembly 501.

Figure 15B:
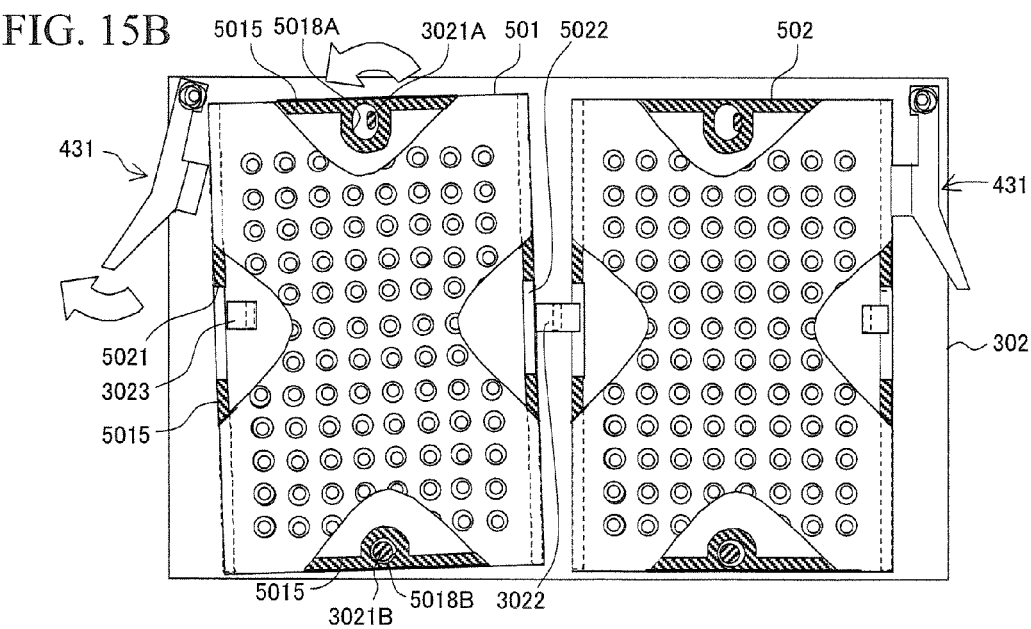

FIG. 15B shows a state in which the pressing portion 433 of the movable hook 431 is thus separated from the outside side surface of the sample plate assembly 501. Then, the sample plate assembly is disposed on the moving stage and made to rotate in the counterclockwise direction (in FIG. 15B). The sample plate assembly is made to rotate on the moving stage until the inside surface of the first concave portion 5018A of the bottom surface of the sample plate assembly 501 abuts on the first convex portion 3021B on the moving stage. As a result, the claw of the outside fixed hook 3023 is detached from the hole 5021 of the outside side surface of the sample plate assembly. Further the claw of the inside fixed hook 3022 is detached from the hole 5022 of the inside side surface of the sample plate assembly. Finally, the sample plate assembly 501 is lifted overall. As a result, the concave portions 5018A and 5018B for positioning of the bottom surface of the sample plate assembly 501 are detached from the convex portions 3021A and 3021B for positioning on the stage, respectively. When the sample plate assembly is mounted, the reverse operation may be performed.

In the embodiment, the sample plate assembly 501 can be accurately positioned on a predetermined position on the moving stage by engaging the convex portion on the moving stage with the concave portion of the bottom surface of the sample plate assembly 501 and pressing the sample plate assembly 501 by the movable hook 431.

In the embodiment, the two sample plate assemblies can be mounted and removed only by rotating the sample plate assembly along a horizontal plane. Further, the mounting operation and the removing operation are the same except that the two sample plate assemblies have opposite rotational directions in operation. Therefore, the two sample plate assemblies can be mounted and removed with one hand.

The invention is not limited to the embodiments. It will be readily apparent to those skilled in the art that various modifications of the invention can be made within the scope of the claims.

What is claimed is:

1. A capillary electrophoresis apparatus comprising:
a capillary in which a capillary head is provided at one end and a capillary anode electrode is formed at the other end; and
an autosampler having a moving stage which transports one or plurality of containers including sample containers to the capillary anode electrode, wherein;
the moving stage has a fixing apparatus for fixing at least a pair of sample containers which are arranged and disposed on the moving stage,
the fixing apparatus has first and second movable hooks and a fixed hook disposed between the first and second movable hooks, the first and second movable hooks each has a projected portion with decreased thickness towards the tip of the projected portion, wherein each of the first and second movable hooks is rotatable around a shaft, the fixed hook has first and second projected portions which are projected on both sides, the fixing apparatus further has a first pair of convex portions disposed between the first movable hook and the fixed hook and a second pair of convex portions disposed between the second movable hook and the fixed hook,
a first sample container having holes on side surfaces of both sides and a pair of convex portions disposed beneath the first sample container, a second sample container having holes on side surfaces of both sides and a pair of convex portions disposed beneath the second sample container,
when the first sample container is disposed between the first movable hook and the fixed hook and the second sample container is disposed between the fixed hook and the second movable hook,
the hole of the outside side surface of the first sample container is engaged with the projected portion of the first movable hook,
the hole of the inside side surface of the first sample container is engaged with the first projected portion of the fixed hook,
the hole of the inside side surface of the second sample container is engaged with the second projected portion of the fixed hook,
the hole of the outside side surface of the second sample container is engaged with the projected portion of the second movable hook,
the first pair of convex portions are engaged with the pair of concave portions disposed beneath the first sample container, and
the second pair of convex portions are engaged with the pair of concave portions disposed beneath the second sample container.

2. The capillary electrophoresis apparatus according to claim 1, wherein the shaft is disposed in a horizontal direction and the movable hook is rotatable along a vertical plane.

3. The capillary electrophoresis apparatus according to claim 1, wherein the shaft is disposed in a vertical direction and the movable hook is rotatable along a horizontal plane.

4. The capillary electrophoresis apparatus according to claim 1, wherein a spring which generates a torque allowing the movable hook to rotate around the shaft is provided, and by the torque, the movable hook is pressed in a direction where a projected portion of the movable hook is engaged with the hole of the outside side surface of the sample containers.

* * * * *